US005521087A

United States Patent [19]
Lee et al.

[11] Patent Number: 5,521,087
[45] Date of Patent: May 28, 1996

[54] METHOD FOR PRODUCING ORIENTED CONNECTIVE TISSUE CELLS IN A LIGAMENT CONFIGURATION

[75] Inventors: Raphael C. Lee, Chicago, Ill.; David Huang, Cambridge, Mass.

[73] Assignee: Massachusetts Institute of Technology, Cambridge, Mass.

[21] Appl. No.: 370,555

[22] Filed: Jan. 9, 1995

Related U.S. Application Data

[63] Continuation of Ser. No. 32,730, Mar. 16, 1993, abandoned, which is a continuation of Ser. No. 349,855, May 10, 1989, abandoned.

[51] Int. Cl.$^6$ ............... A61F 2/06; A61F 2/08; A61F 2/10; C12N 5/02
[52] U.S. Cl. ............ 435/240.2; 435/174; 435/240.23; 623/1; 623/13; 623/16
[58] Field of Search ................ 435/174, 240.2, 435/240.23; 623/1, 13, 16

[56] References Cited

U.S. PATENT DOCUMENTS

| | | | |
|---|---|---|---|
| 4,458,678 | 7/1984 | Yannas et al. | 435/240.2 |
| 4,485,096 | 11/1984 | Bell | 424/95 |
| 4,485,097 | 11/1984 | Bell | 424/95 |
| 4,539,716 | 9/1985 | Bell | 424/95 |
| 4,546,500 | 10/1985 | Bell | 424/95 |

OTHER PUBLICATIONS

Bell, E., et al., *PNAS USA*, 76(B): 1274–1278 (1979).
Weinberg, C. G., and Bell, E., *J. Cell Physiol.* 122: 410–414 (1985).
Ehrlich, H. T., *J. Cell Sci.*, 82: 281–294 (1986).
Weinberg, C. B. and Bell, E., *Science*, 231: 397–400 (1986).
Aggarwal, A., A Syngeneic Ligament Equivalent, Phase I: Mechanical . . . Lattice, S. B., Thesis M.I.T.

*Primary Examiner*—David M. Naff
*Assistant Examiner*—L. Blaine Lankford
*Attorney, Agent, or Firm*—Hamilton, Brook, Smith & Reynolds

[57] ABSTRACT

The present invention pertains to an oriented tissue-equivalent formed by contracting a collagen solution with connective tissue cells. In the method of the present invention, the contraction of collagen fibrils by the connective tissue cells is restrained along an axis of cell alignment defined by at least two structural members within the gel, whereby the connective tissue cells align along the axis thereby producing an oriented tissue-equivalent. In a preferred embodiment fibroblast cells are used to contract a collagen gel to form connective tissue into a ligament configuration.

5 Claims, 16 Drawing Sheets

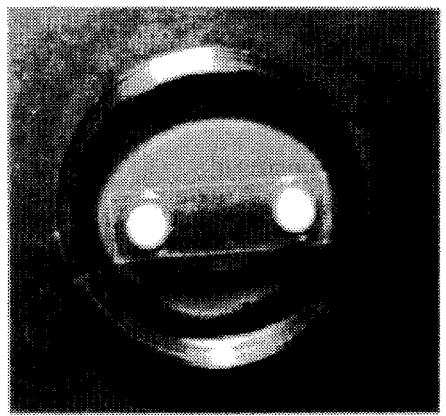
FIG. IA
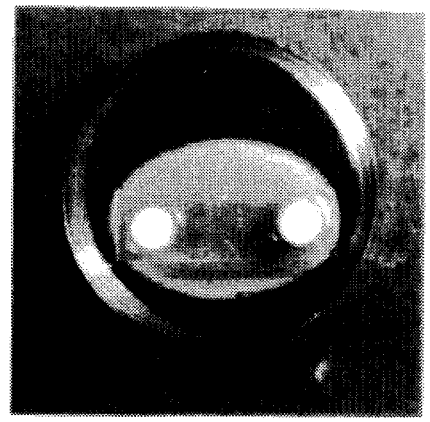
FIG. IB
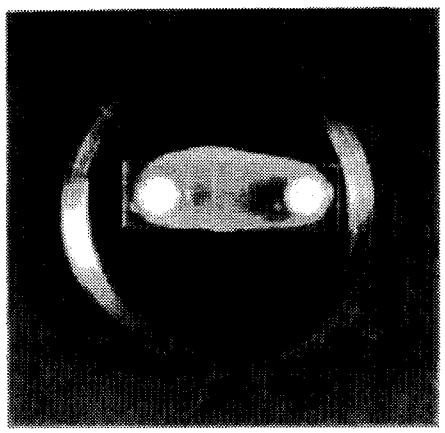
FIG. IC
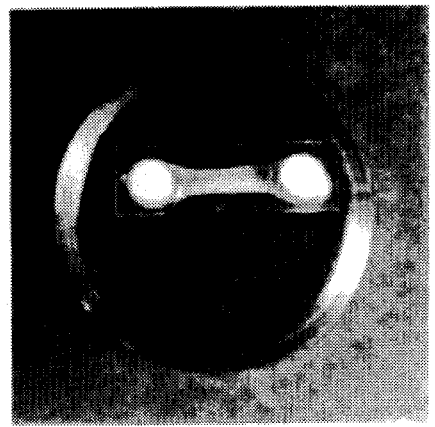
FIG. ID

METHOD FOR PRODUCING ORIENTED CONNECTIVE TISSUE CELLS IN A LIGAMENT CONFIGURATION

This application is a continuation of application Ser. No. 08/032,730 filed Mar. 16, 1993, now abandoned, which is a continuation of Ser. No. 07/349,855 filed May 10, 1989, now abandoned.

BACKGROUND OF THE INVENTION

The functional properties of soft connective tissue are determined by the content and organization of connective tissue cells and extracellular matrix. The connective tissue cells are responsible for the synthesis, organization, and breakdown of the extracellular matrix. Collagen and elastin fibers together comprise the fibrous component of the extracellular matrix and function as the major load-bearing elements for tensile stress. Elastin is a relatively low-modulus material that in some tissues determines the elastic properties at lower strains. Collagen fibers have a higher modulus, are more abundant, and provide most of the tensile strength. In tendons and ligaments, where large tensile forces are transmitted along the longitudinal axis, collagen fibers are densely packed in arrays parallel to the tensile load. In skin and fascia, collagen fibers are more diffusely oriented, although a preferred orientation may exist depending on mechanical demand. Both collagen and elastin fibers are stengthened by intermolecular covalent crosslinks.

The extracellular matrix is also characterized by a non-fibrous component comprised of proteoglycans and glycoproteins. Proteoglycans are composed of a protein core attached to various glycosaminoglycan side chains and contain numerous negatively charged sulfate and carboxyl groups. By their ability to produce high osmotic swelling pressure, these ionized groups are the source of a large component of the compressive modulus in connective tissue. Proteoglycans are found in all connective tissue, but are particularly abundant in cartilage and in segments of tendon that are subjected to large compressive forces.

Ligaments are a highly organized load-bearing connective tissue containing collagen fibers and fibroblasts primarily ordered in a parallel array, giving them a flexible yet strong mechanical character. The fibroblasts, which sparsely populate the ligament, are spindle shaped and form intercellular cytoplasmic connections. The collagen fibers are densely crosslinked and oriented in the direction of the mechanical stress. As a result, ligaments are strongest and stiffest in the direction of the mechanical stress.

Tendons are the connective tissue connecting muscles with mobile structures such as bones, cartilages, ligaments, and fibrous membranes. Tendons are white, glistening fibrous cords of various dimensions and considerable strength. They consist almost entirely of white fibrous tissue and collagen fibrils which are oriented parallel to each other and firmly united together. The larger tendons are supplied with blood vessels and nerves.

Some connective tissue has the ability to repair itself and adapt to changes in mechanical demands. During the normal growth pattern and repair of damaged tissue, cellular activities in connective tissue are greatly accelerated and parallel changes in structure and function are observed. For example, the healing of ligament tissue due to an injury can be divided into three phases: inflammation, matrix and cellular proliferation, and remodeling and maturation. Woo, S. L. Y. and Buckwalter, J. A., Eds., *Injury and Repair of the Musculoskeletal Soft Tissues,* American Academy of Orthopedic Surgeons, Park Ridge, Ill. (1988). Immediately following the disruption of a ligament, the wound site is rapidly filled with clotting blood. Increased vascular permeability causes serous fluid to accumulate and the surrounding tissue to become edematous. Within a few hours, lymphatic cells migrate into the injury site. Subsequently, numerous fibroblasts appear in the wound bed and produce extracellular scar matrix.

Cell and matrix proliferation results in the formation of a highly vascular granulation tissue between the ends of the torn ligament. The tissue is highly cellular, as shown by histology and DNA content, with fibroblasts being the dominant cell type. Collagen turnover, both in terms of synthesis and degradation peaks in the early part of this phase. The collagen synthesized is predominantly type I. The glycosylaminoglycan content is elevated and the water content is higher than normal.

Under polarized light, the extracellular matrix initially appears disorganized and highly cellular. With time, both the composition and organization of the scar tissue continues to approach that of normal tissue. Further, the mechanical strength of the scar tissue increases during this period in response to the mechanical environment, and in some cases can approach that of uninjured tissue.

Both ligament and tendon injuries to the hand, wrist and knee are common clinical problems. For example, injuries of the knee account for about 60% of the cases. Ligament injuries can be classified into three categories: sprain, over-stretching (partial rupture), and rupture. Over 80% of ligament injuries can be treated using non-invasive methods such as rest, ointments, elastic bandage, aspiration, or cast. More severe injuries require surgical treatment involving suturing detached or ruptured components. In these cases, success rates of complete healing and reconstruction range from about 60% for the posterior cruciate ligament to about 16% for the anterior cruciate ligament.

Seriously damaged ligament tissue can be replaced by prosthetics or transplantation of autogenous tissue. Prosthetic ligaments currently being investigated in the United States are the Polyflex® ligament and the Proplast® ligament. However, these synthetic, biopolymeric materials have not produced satisfactory long term results.

In addition, transplantation of autogenous tissue and tendon transfers have yielded disappointing results. Autogenous corium grafts for the repair of injured collateral knee joint ligaments result in full restoration of stability for about 60% of all cases. However, for the anterior cruciate ligament, autogenous corium grafting proves to be effective for less than 20% of all cases. The effect of autogenous grafts has the further disadvantage of traumatizing uninjured tissues.

Thus, there is a critical need for the development of a more effective method, technique, and material for the reconstruction or replacement of injured ligaments and other connective tissue, such as tendons, skeletal muscle and cardiac muscle.

SUMMARY OF THE INVENTION

This invention pertains to a method for producing an oriented tissue-equivalent comprising forming a collagen gel having living connective tissue cells dispersed therein. The cells are capable of contracting the gel. The gel is maintained under conditions suitable for contraction by the connective tissue cells, while simultaneous contraction of the gel is restrained to define an axis of predetermined length for cell alignment. The connective tissue cells align along the defined axis to produce an oriented tissue-equivalent having increased mechanical strength in the direction of the axis.

In one embodiment, the contraction of the collagen gel by the connective tissue cells is restrained along an axis defined by two structural members. Preferably, the structural members which define the axis and restrain the contraction of the collagen gel are posts spaced a predetermined distance apart. These posts restrain the contraction of the collagen gel such that the connective tissue cells align along the axis defined along a line joining the two posts, thereby forming an oriented tissue-equivalent having improved mechanical strength in the direction of the axis.

The present invention further pertains to a mechanical testing apparatus useful for determining the mechanical properties of an oriented tissue-equivalent, while simultaneously providing a suitable cell culture environment. The mechanical testing apparatus comprises an incubator equipped with means for controlling the atmosphere and means for controlling the temperature inside said incubator. Located within the incubator chamber are means for securing, in a desired location, the oriented tissue-equivalent to be mechanically tested. Further, the apparatus is equipped with means for controlling the length of the oriented tissue-equivalent, means for determining the force generated by the oriented tissue-equivalent, means for determining the length of the oriented tissue-equivalent and means for conditioning and recording force and length measurements.

The oriented tissue-equivalent of the present invention can be used to replace damaged connective tissue, for example ligaments, tendons, skeletal and cardial muscle, and has several advantages over nonliving artificial materials. Unlike nonliving synthetic materials which provide a poor surface for immune cells to adhere, the oriented tissue-equivalent is accessible to and can be protected by the immune system. The oriented tissue-equivalent is a living tissue, thus having the ability to respond to physiological demands and to repair itself. Further, integration of the oriented tissue-equivalent with the host tissue improves with time.

BRIEF DESCRIPTION OF THE DRAWINGS

FIGS. 1A–1D are photographs depicting the contraction process of a collagen gel by the fibroblasts in the formation of an oriented tissue-equivalent in the form of a ligament.

DETAILED DESCRIPTION OF THE INVENTION

Figure 2:
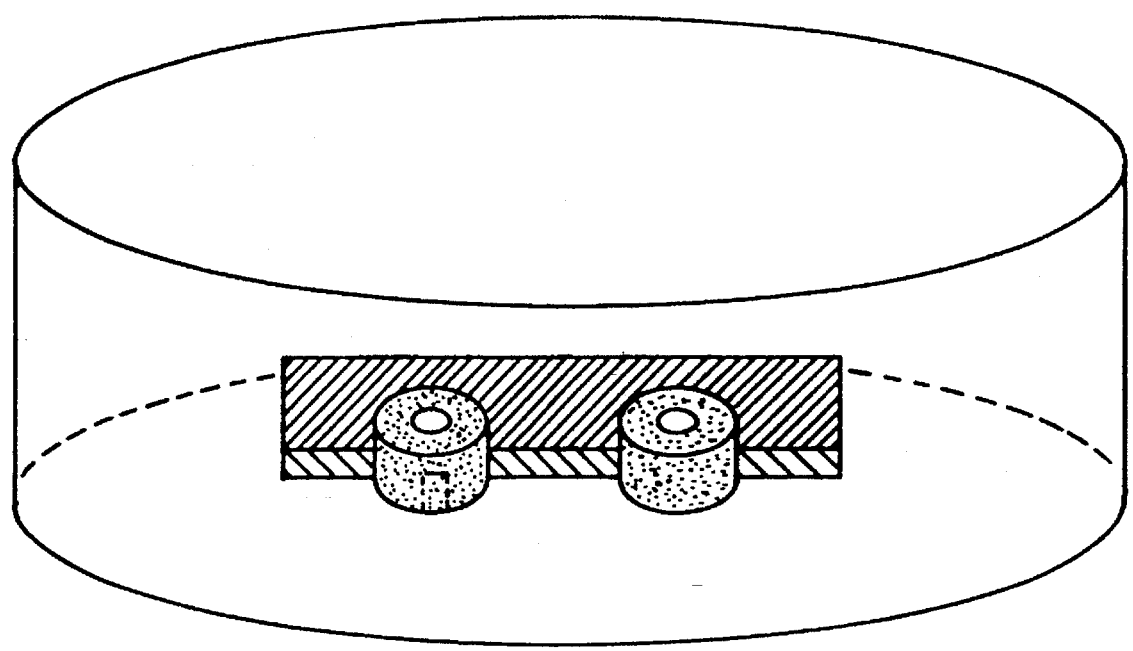
FIG. 2 is an illustration of a culture dish having porous polyethylene posts and a spacer around which an oriented tissue-equivalent can be formed.

An oriented tissue-equivalent is defined herein as a material which is formed in vitro with living cells and proteinaceous fibers, is uniaxially aligned (e.g., to thereby increase mechanical strength along the alignment axis), and has mechanical and physiological properties similar to in vivo oriented tissue.

The formation of tissue-like structures from fibroblasts and other contractile agents which contract reconstituted collagen gels have been previously described. See U.S. Pat. No. 4,485,096. It was reported that fibroblasts can condense a hydrated collagen lattice to a tissue-like structure 1/28th the area of the starting gel in 24 hours. This process is believed to parallel that which occurs in vivo in the course of wound contraction, whereby cells interact with protein fibers, such as collagen.

Further, collagen lattices seeded with fibroblasts and keratinocytes have been used to produce a skin-equivalent tissue. See U.S. Pat. No. 4,485,096. It was reported that living skin-equivalent grafts were successfully grafted onto the donors of the cells. These grafts became well vascularized, incorporated into the host, and inhibited wound contraction.

The first step in the formation of an oriented tissue-equivalent comprises forming a collagen gel having connective tissue cells dispersed therein. The collagen useful in forming the gel can be extracted from various collagen-containing animal tissue. Examples of possible collagen-containing tissue are tendon, skin, cornea, bone, cartilage, invertebral disc, cardiovascular system, basement membrane and placenta. The collagen used herein is type I collagen derived from rat-tail tendon. Other types of collagen (e.g., type III) may also be employed. Conditions whereby collagen can be extracted from are: 1) low ionic strength and neutral buffer; 2) weak acid solution; and 3) partial pepsin digestion followed by extraction in acid solution. For example, the collagen can be derived by acid extraction followed by salt precipitation of rat tail collagen from acid solution. By avoiding the use of pepsin, collagen retains intact telo-peptides and the ability to form lysine-derived covalent crosslinks.

The connective tissue cells useful to contract the collagen fibrils in the formation of an oriented tissue-equivalent can be obtained from various mammalian sources (e.g., bovine, porcine, human, canine). Examples of possible connective tissue cells are fibroblasts, smooth muscle cells, striated muscle cells and cardiac muscle cells. The connective tissue cells used in the method of the present invention were human foreskin fibroblasts, but other types, such as bovine fibroblasts may also be employed. The human foreskin fibroblasts can be obtained by trypsin disaggregation.

The isolated collagen and connective tissue cells can be cultured in a medium which provides nutrients to support cell growth, for example, Dulbecco's Modified Eagle Medium (DMEM). Additional components can be added to the medium to enhance collagen synthesis and crosslinking and cell growth and viability, for example fructose (in the absence of glucose), ascorbic acid, TGF-β (a growth factor), and gentamicin (an antibiotic). Further, components which are desirable for collagen crosslinking such as copper and pyridoxal (cofactors of lysyl oxidase) and lysyl oxidase (an enzyme) can also be added to the medium.

In the formation of a collagen gel, the mixture of collagen and connective tissue cells in a media as described above, is placed in a biocompatible container in which cells can be cultured, such as a petri dish. The dish can be coated with a water repellant to retard cell adhesion, such as organosilane.

At a slightly elevated temperature, the mixture of collagen and connective tissue cells will gel, corresponding to the precipitation of collagen molecules into fibrils. For example, with the collagen and fibroblasts used herein, warming of the mixture to about 37° C. is sufficient to induce collagen precipitation. The gels are then maintained under standard cell culture conditions well established in the art, suitable for contraction of the gel by the connective tissue cells. Over time, the cells consolidate and organize the collagen fibrils producing macroscopic contraction of the gel. The oriented tissue-equivalent is formed as the embedded connective tissue cells contract the gel by attaching to and pulling together collagen fibers.

In the method of the present invention, the contraction process is restrained along an axis of predetermined length, defined by at least two structural members spaced a distance apart. The connective tissue cells align along the axis defined along the line joining the two structural members, to thereby produce an oriented tissue-equivalent having increased mechanical strength in the direction of the axis.

Structural members which can be used to restrain the contraction process of the collagen fibrils by the connective tissue cells can be of various shapes, diameter and height and can be easily accomodated within the dimensions of the culture dish. The structural members can be spaced a predetermined distance apart to provide an axis along which the cells can align the collagen fibrils. For example, the structural members can be cylindrical posts, spherical objects such as pellets, and rectangular bars. Further, the structural members can be formed of a biocompatible material, such as polyethylene or hydroxyapatite, and can be porous. The pore size of the structural members can be about a few hundred microns to allow for cell attachment and growth within and around the member.

In one embodiment, as shown in FIG. 2, the structural members are porous posts (#5531 Porex, Fairburn, Ga.) of a porosity of 35 microns which allows for cell growth within the posts. The posts are positioned in the center of the culture dish. An axis is defined as the line joining the two posts along which the cells can align. The posts are positioned a fixed distance apart, for example approximately 2 cm, and restrain the contraction process of the gel by the cells to form an oriented tissue-equivalent around and between the posts having a "dumbbell shape". The contraction process aligns or orients the connective tissue cells along the direction in which contraction is restrained which in this configuration is parallel to the axis joining the two posts. FIGS. 1A–1D depicts this contraction process. In this configuration, the oriented tissue-equivalent can be easily implanted in an individual. For example, a damaged ligament which joins two bones can be replaced with the oriented tissue-equivalent. Holes can be drilled in the bones through which the porous posts, having the oriented tissue-equivalent formed around and between them, can be inserted. The posts can be composed of polyethylene or similar material and therefore, are biocompatible to avoid immune rejection, and can be porous, to allow for continued cell growth within the posts and surrounding bone and tissue. Preferably, the posts are formed of hydroxyapatite which is the primary mineral constituent of bone, and therefore would be both compatible and porous when inserted in a bone as described above. Further, hydroxyapatite is known to enhance bone regeneration and bone growth.

Figure 5:
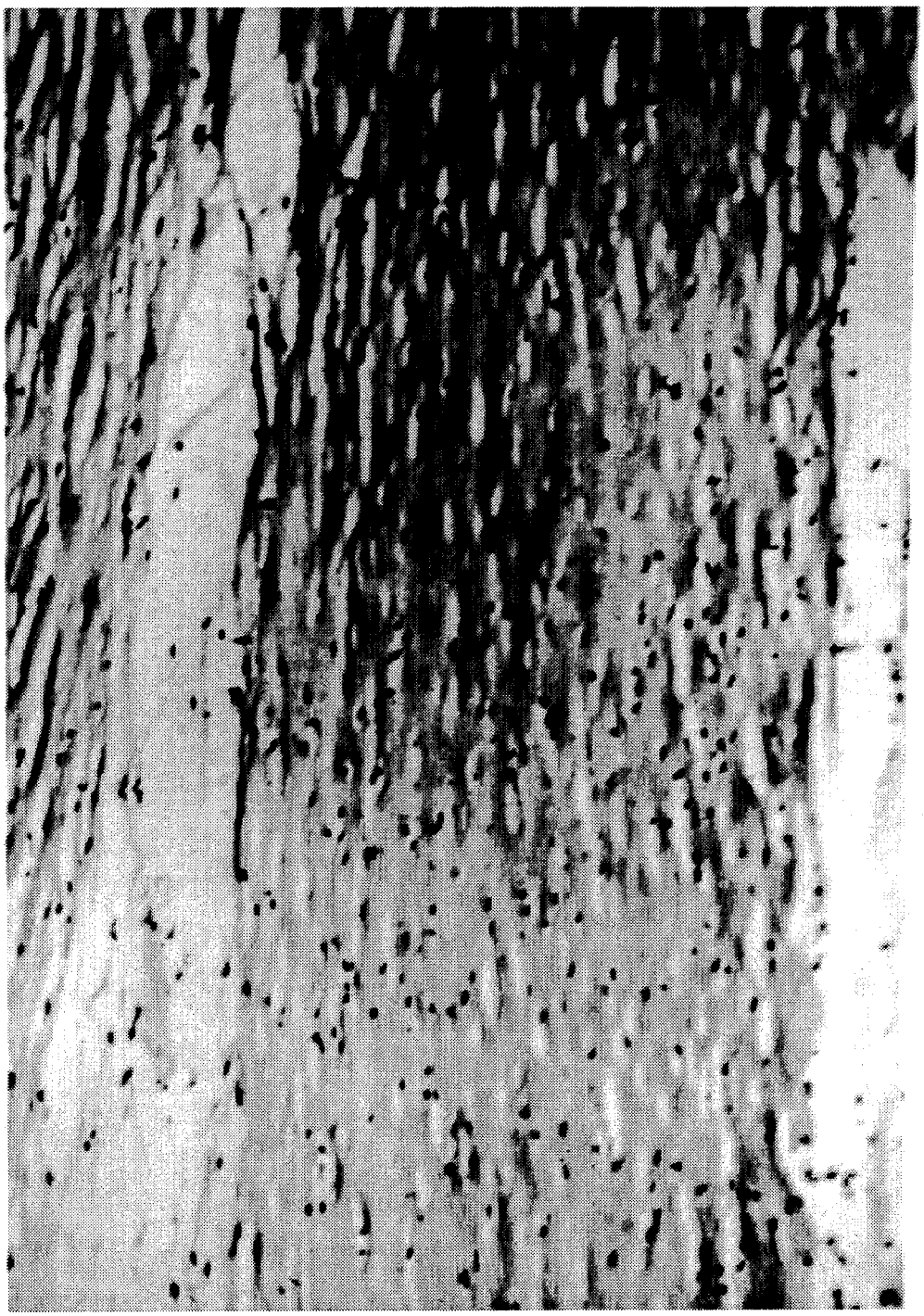
FIG. 5 is a photomicrograph of an H & E section of an oriented tissue-equivalent depicting the alignment of cells along the circumferential axis.

A section of Hematoxylin and Eosin (H & E) stained gel (FIG. 5) shows the parallel orientation of the fibroblasts in the oriented tissue-equivalent. This alignment of cells is an important feature of the oriented tissue-equivalent and of ligaments and tendons in general, where the orientation of cells and matrix make the tissue strongest and stiffest in the direction of tensile load.

The pattern of cell alignment is consistent with the belief that cells are able to orient by matrix rigidity. Lackie, J. M., *Cell Movement and Cell Behavior*, Allen & Unwin, Boston, (1986). As cells exert traction on the collagen matrix, the matrix becomes consolidated in the unconstrained axes. However, along the axis between the two rigid posts, the cells align the matrix which stiffens, and provides cells an orientation cue. In the periphery of the oriented tissue-equivalent, cell alignment is not observed due to relatively unrestrained matrix compaction in all dimensions. In the center of the oriented tissue-equivalent, where matrix compaction is rigidly constrained along one axis, uniform cell alignment is observed. These results suggest that to obtain a uniform oriented tissue-equivalent, the initial diameter of the reconstituted collagen gel should be small relative to the distance between the two posts.

As described in detail in the examples, several aspects of the oriented tissue-equivalent such as cell number and matrix compaction, reached a steady state after 2 to 3 weeks in culture. The dry weight of the oriented tissue-equivalent changed very little over time, suggesting that degradation and biosynthesis of extracellular matrix are either very slow or are in very close balance.

To characterize the mechanical properties of the oriented tissue-equivalent formed by the method of the present invention, the oriented tissue-equivalent was maintained in an incubator-mechanical testing apparatus specially designed to control temperature, gas composition, and recirculate culture media.

Figure 3:
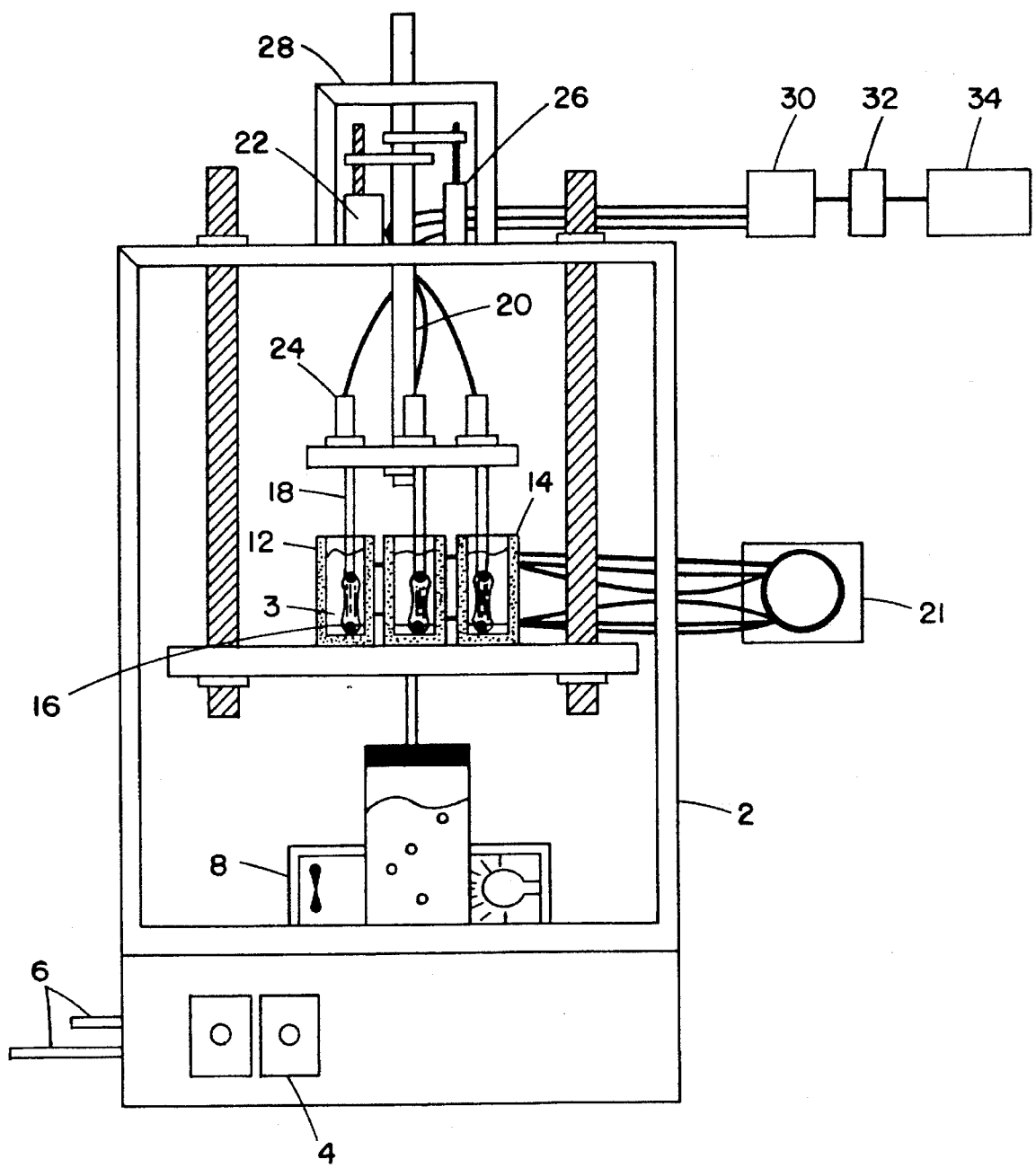
FIG. 3 is an illustration of the mechanical testing apparatus of the present invention.
Figure 4:
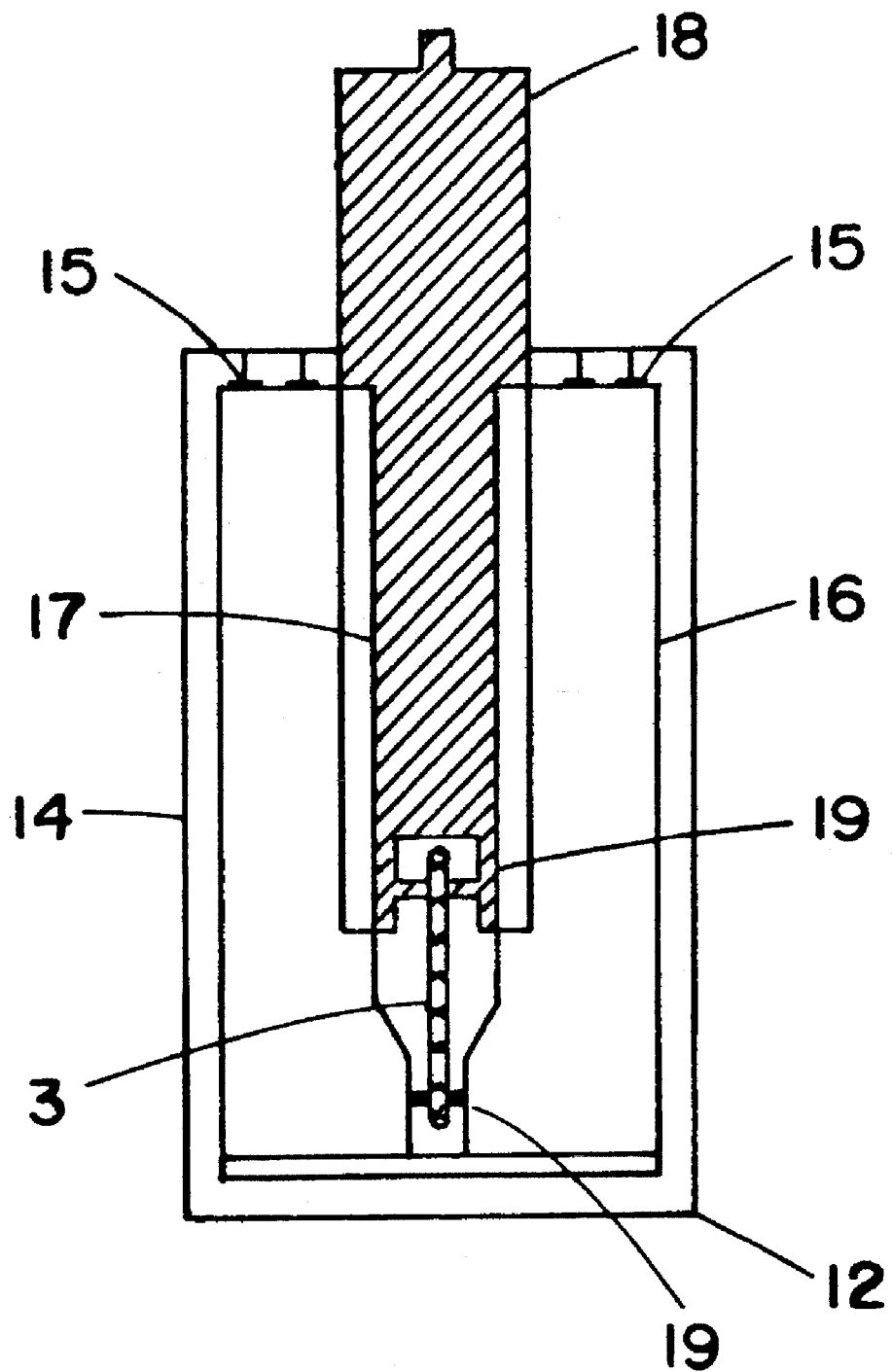
FIG. 4 is an illustration of the loading chamber of the mechanical testing apparatus.

The mechanical testing apparatus is illustrated in FIGS. 3 and 4. An incubator 2 is equipped with means to control the internal composition of the atmosphere, such as flowmeters 4 and gas tubes 6. A means for controlling the incubator temperature, such as a heating convection unit 8 is located at the base of the incubator 2.

A means for securing an oriented tissue-equivalent 3 within the apparatus, for mechanical testing is shown in FIG. 4. An oriented tissue-equivalent 3 is placed in a loading chamber 12. The loading chamber 12 is comprised of an outer vessel 14, an inner vessel 16, and a shaft 18 and is connected to a peristaltic pump 21, for recirculating culture medium (see FIG. 3). The outer vessel 14, which contains the culture medium, surrounds the inner vessel 16 and shaft 18. The inner vessel 16 is secured to the outer vessel 14 with screws 15. The inner vessel 16 has an inner chamber 17 in which shaft 18 resides. The dimensions of inner chamber 17 substantially match those of shaft 18. One end of the oriented tissue-equivalent 3 is secured to inner vessel 16 by a securing means 19 and the opposite end of the oriented tissue-equivalent 3 is attached to shaft 18 by similar securing means 19. The opposite end of shaft 18 is connected to an actuator 20 which is in turn connected to a means for controlling the length of the oriented tissue-equivalent, a computer controlled step motor 22. Thus, the connection of the oriented tissue-equivalent 3 to the actuator 20 provides a direct connection for the stretching or compressing of the oriented tissue-equivalent 3.

Further, a force transducer or load cells 24, means for determining the force generated by the oriented tissue-equivalent, are connected to the actuator 20 and the shafts 18 of the loading chamber 12. A linear variable differential transformer (LVDT) 26, means for determining the displacement of the actuator 20, and thus, the length of the oriented tissue-equivalent 3 is housed in a case 28 at the top of the apparatus. The LVDT 26 and load cells 24 are connected to an electronic amplifier 30 which amplifies the forces and length signals and to an analog-to-digital converter 32, which converts the force and length signals to 12 bit quantities which can be recorded on a computer 34.

When secured in the mechanical testing apparatus, an oriented tissue-equivalent and part of the drive shaft to which it is attached are immersed in culture media. Displacement of the drive shafts produces a change in the buoyant forces on the drive shafts. Thus, in the mechanical testing of the oriented tissue-equivalent, these forces are measured and substracted from the tensile load recording.

Figure 6:
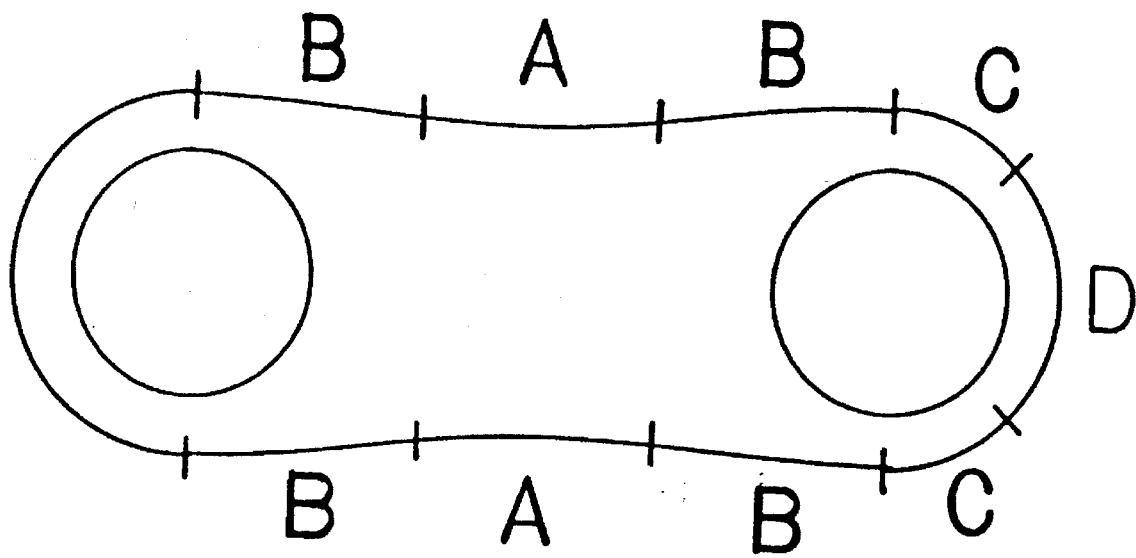
FIG. 6 is a schematic representation of an oriented tissue-equivalent. A, B, C, and D designate regions within the oriented tissue-equivalent of different tensile strength.

As shown in FIG. 6, as an oriented tissue-equivalent forms, the tissue curves around and is adherent to the polyethylene posts. Thus, the tensile strain in the curved regions C and D is expected to be less than in the linear regions A and B between the two posts. With the assumption that only the linear region is subject to tensile strain, the length of the oriented tissue-equivalent material being tested as described in the following examples, is defined as the distance between the two posts. The initial distance of 2 cm between the two posts is defined as the resting length, and nominal strain values are calculated based on these definitions.

Figure 7:
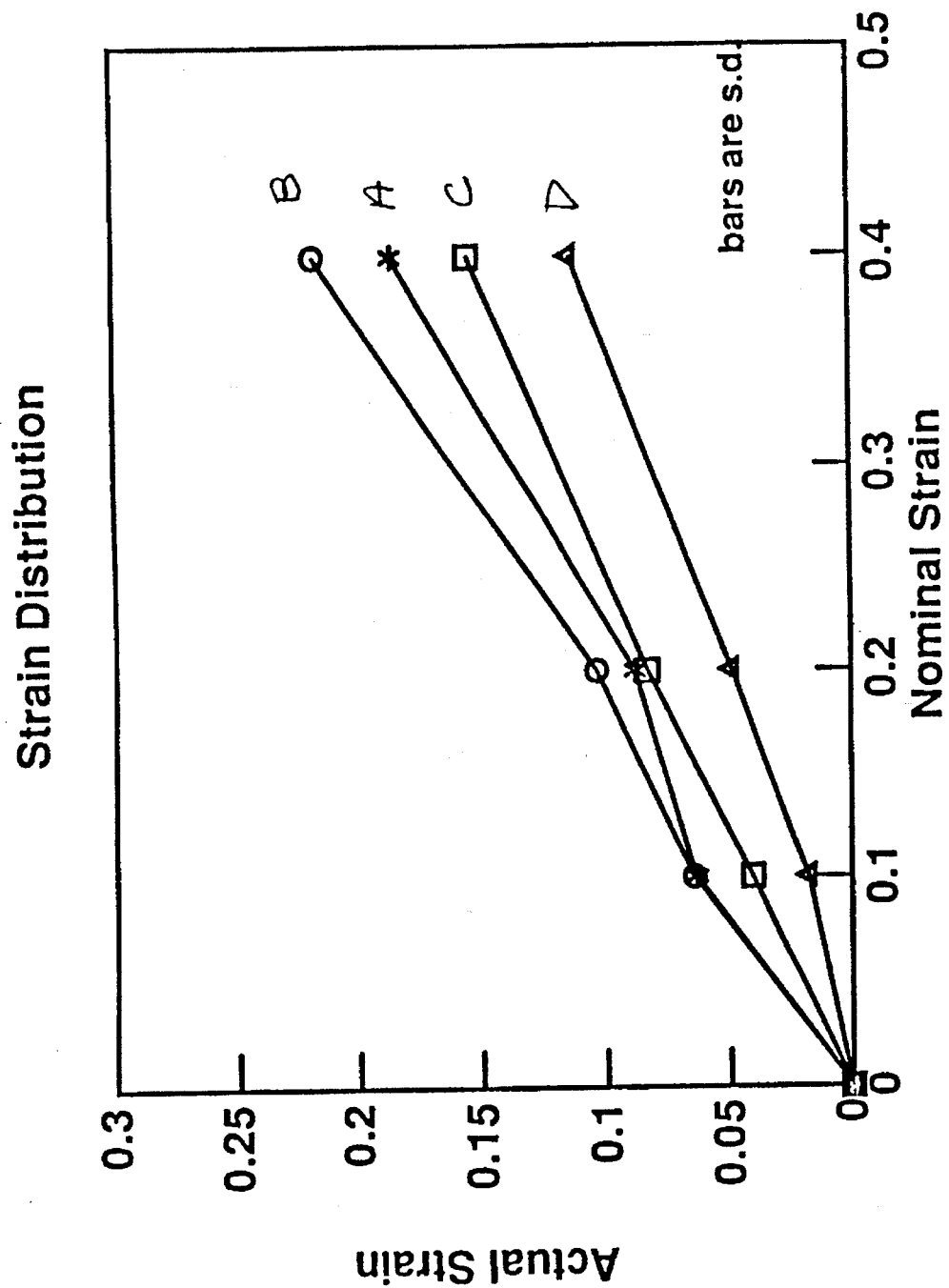
FIG. 7 is a graphic representation of strain distribution, nominal versus actual, in an oriented tissue-equivalent with A, B, C, and D corresponding to regions depicted in FIG. 6.

The actual strain distribution in the oriented tissue-equivalent is tested by placing markers (fine suture) at fixed intervals along oriented tissue-equivalent samples and optically tracking the displacement of these markers at various nominal strains. FIG. 7 plots the optically determined strain in different regions of the oriented tissue-equivalent versus the nominal strain. Although tensile strains in the curved regions are smaller than in the linear regions, they are not insignificant. The greatest amount of strain occurs in region B, where cross-sectional area is expected to be smaller due to the initial circular geometry of the oriented tissue-equivalent at casting. The strain in this area is approximately 60% of the nominal strain therefore, the nominal strain at failure may be up to 70% higher than the actual strain at failure, and the incremental Young's modulus calculated using the nominal strain is approximately 40% lower than the actual modulus of the oriented tissue-equivalent material. Data presented in the following examples are nominal values.

The typical load-strain curve of an oriented tissue-equivalent that has been cultured for 6 weeks is shown in FIG. 7 and described in detail in Example III. The breaking strength is defined as the maximum tensile load measured as an oriented tissue-equivalent is stretched at a constant rate until it is physically disrupted. Matrix synthesis, and intrafiber and interfiber crosslinking of collagen are expected to have a major influence on the breaking strength. The slope of this curve between 5–6% strain is determined by linear regression and defined as the incremental stiffness in that strain range. Tensile strength and incremental Young's modulus is obtained by dividing the breaking strength and incremental stiffness by the estimated cross-sectional area of the oriented tissue-equivalent. Cross-sectional area is estimated by dividing the volume of the oriented tissue-equivalent by the resting length (3.1 cm, which includes 2.0 cm in the linear region and 1.1 cm in the curved region). The volume of the oriented tissue-equivalent is obtained from the wet weight, assuming the density to be 1.0 gram/ml.

Figure 8:
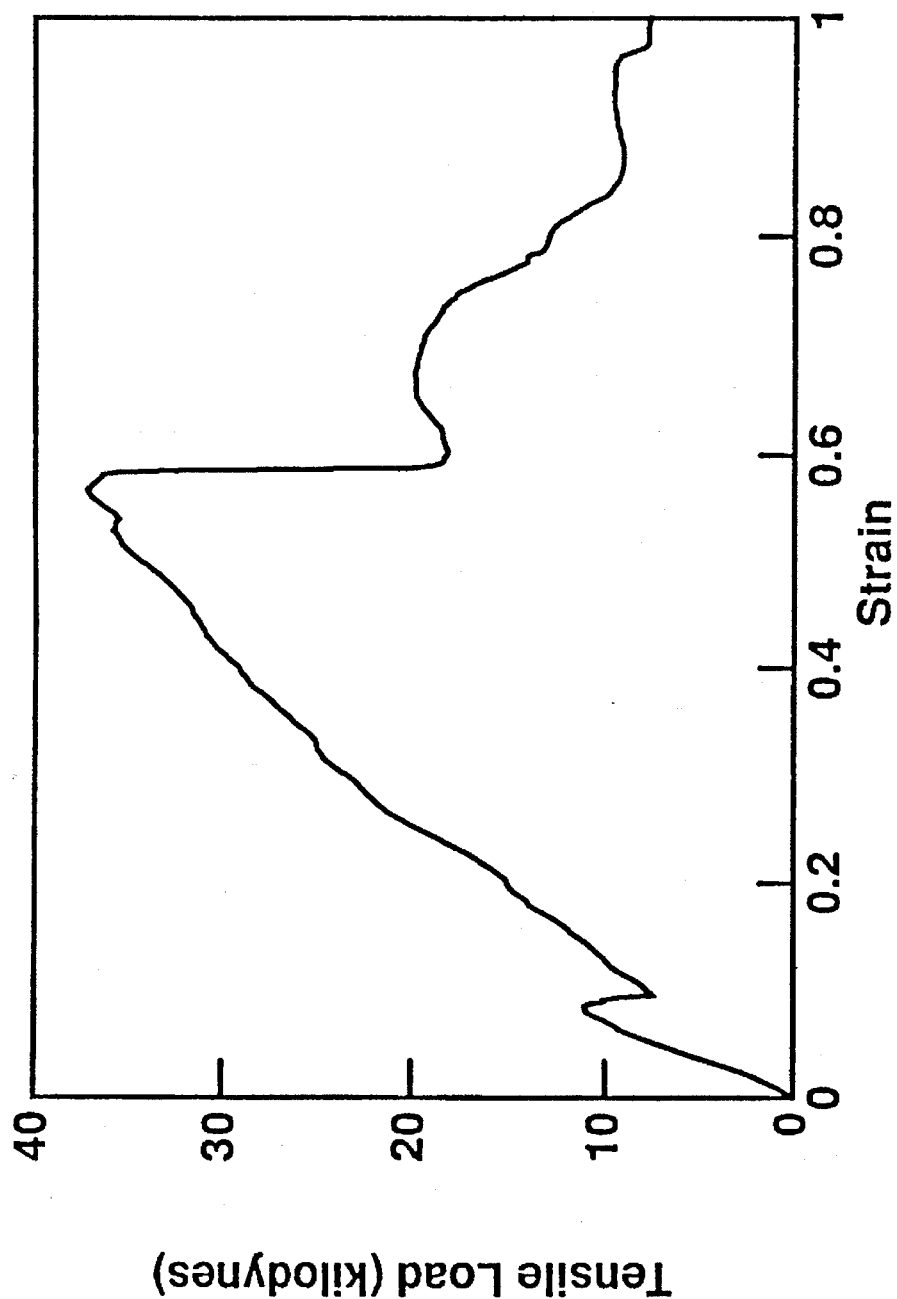
FIG. 8 is a graphic representation of a typical load-strain curve of an oriented tissue-equivalent after six weeks in culture.

FIG. 8 shows that prior to failure, there are several local minima of the load-strain curve, where the oriented tissue-equivalent seems to be starting to fail but then recovered at higher strain. These minima may have been caused by yield in some parallel component of the oriented tissue-equivalent that does not disrupt the entire specimen mechanically. This reflects nonuniformity in the organization of the matrix in the oriented tissue-equivalent. Collagen fibers that are initially oriented with the axis of tensile load and have a higher prestress are expected to become load-bearing at lower strain and to yield at lower strain. Collagen fibers that are not initially aligned with the axis of tensile load become aligned at a higher strain and also yield at a higher strain. Nonuniformity in orientation and prestress may be inherent in the contraction process that forms the oriented tissue-equivalent. Furthermore, the geometry in which the collagen gel is initially cast may further accentuate the nonuniformity. The collagen gel is initially cast in a thin circular sheet. The periphery is relatively unconstrained by the central posts in the early stages of contraction. Unconstrained contraction can be expected to be uniform along all axes. Contraction of the more central portion of the gel is constrained in the circumferential direction by the two fixed posts, and collagen fibers should become oriented in that direction. Histological sections show that the peripheral portion of the oriented tissue-equivalent is less oriented than the central portion.

As described in detail in the examples, the mechanical strength of the oriented tissue-equivalent continues to increase at least up to the sixth week in culture, as evidenced by the increases in tensile load at failure, estimated tensile stress at failure and estimated incremental Young's modulus. Several possible explanations are the continued covalent crosslinking of the reconstituted collagen matrix, de novo synthesis and organization of collagen and elastin by the embedded cells, or secretion of glycoproteins that stabilize the reconstituted collagen matrix in its compacted geometry.

The stress-strain relationship of the oriented tissue-equivalent is highly nonlinear like other soft connective tissues and reflects its nonhomogeneous composition. The characteristic stress-strain relationship of soft connective tissue has a "toe region" of low modulus at low strain. The tissue gradually stiffens at higher strain and reaches a "linear region" where the modulus is roughly constant. At higher strain the tissue yields. The strain-stiffening is generally attributed to the straightening out of wavy collagen fibers and the alignment of collagen fibers along the axis of strain.

The incremental Young's modulus of the oriented tissue-equivalent is measured in the strain range of 5–6% because in this range the typical oriented tissue-equivalent has reached the "linear region" and has yet not begun to yield.

At the end of 6 weeks in culture, the mechanical properties of the oriented tissue-equivalent have not yet reached a steady state. This is not surprising when compared with the rate with which the tensile strength of wounds approach steady state in vivo. The tensile strength of disrupted canine medial collateral ligament is ½ of the value of intact tendon after 12 weeks and ⅔ after 48 weeks. Woo, S. L. Y., et al., *Am. J. Sports Med.*, 15: 22–29 (1987). Further, the tensile strength of skin wound reach ½ of that of intact skin after roughly 5 weeks, and ⅔ after 12 weeks. Forrester, J. G., et al., *J. Trauma*, 10: 770–779 (1970).

Table I shows that at 6 weeks, the tensile strength and incremental modulus of the oriented tissue-equivalent are much lower than that of skin or ligament by 2 to 3 orders of magnitude. The strain at failure of the oriented tissue-equivalent is in between that of skin, a tissue with non-oriented collagen fibers, and that of tendon, a parallel-fibered tissue.

TABLE I

| Tissue Type | Oriented Tissue-Equivalent | Skin | Tendons | Ligament |
|---|---|---|---|---|
| Tensile Strength (MPa) | 0.07 | 4–14 | 10–95 | 70 |
| Strain at Failure | 0.58 | 0.8–1.0 | 0.06–0.45 | |
| Incremental Modulus (MPa) | 0.31 | 1–44 | 39–1000 | 700 |

To determine the effect of intramolecular and intermolecular crosslinking of collagen molecules on an oriented tissue-equivalent, several gels where cultured in the presence of BAPN, a drug which interferes with collagen crosslinking. Covalent crosslinking between collagen and elastin molecules is important for the strength of collagen and elastin fibers in vivo. Collagen molecules are able to assemble themselves into fibers with a characteristic 4D stagger structure under appropriate conditions, presumably by charged and hydrophobic interactions between molecules. However, covalent bonds are needed to stabilize the fiber structure. Lysyl oxidase is the enzyme that initiates covalent crosslinking of collagen and elastin. Two cofactors, copper and pyridoxal, are needed for the activity of lysyl oxidase.

BAPN (β-aminopropionitrile) binds to and irreversibly inactivates lysyl oxidase. The mechanism of inactivation appears to be one in which BAPN binds to the active site and is then enzymatically converted to a chemically reactive species which covalently derivatizes the enzyme. Kagan, H. M., *Regulation of Matrix Accumulation*, (Ed. Mecham, A. P.) Acadamic Press, N.Y. (1986). By inhibiting lysyl oxidase, BAPN prevents the formation of lysine-derived crosslinks in collagen. It has been widely used to induce pathologic conditions in animals known as lathyrism, characterized by fragility of bones, skin and blood vessels, hyperextensibility of skin, and reduced muscle mass. Pasquali-Ronchetti, I., et al., *Exp. and Molecular Path.*, 35: 42–56 (1981).

As described in detail in Example V, oriented tissue-equivalent cultured in the presence of 0.5 mM BAPN had much lower breaking strengths (19% of control), and significantly lower dry weights (80% of control) than control specimens after 21 days of culture. The results show that fibroblasts in the oriented tissue-equivalent are able to synthesize and secrete lysyl oxidase and that this lysyl oxidase activity is essential to the increase in breaking strength and incremental Young's modulus during long term culture.

The oriented tissue-equivalents were cultured in the presence of transforming growth factor type β, (TFG-β), to determine the degree to which TFG-β increases extracellular matrix biosynthesis and thereby increases the mechanical strength in the oriented tissue-equivalent. As described in detail in Example VI, oriented tissue-equivalents were cultured in the presence of TFG-β and the incorporation of protein and sulfated glycosaminoglycan into the extracellular matrix were measured with radiolabels.

The results show that addition of TFG-β into the culture media for the oriented tissue-equivalent increases the incorporation of protein and sulfated glycosaminoglycan into the extracellular matrix and is likely to accelerate the increase in mechanical strength of oriented tissue-equivalents in long term culture.

The following examples describe in detail the numerous procedures and techniques used in the formation of the oriented tissue-equivalent and the determination of its mechanical properties. These examples are not to be considered limiting in any way.

EXAMPLE I: Formation of an Oriented Tissue-Equivalent

Human Fibroblast Primary Cultures

The fibroblasts in the oriented tissue-equivalents were harvested from human neonatal foreskin fibroblasts. To isolate human foreskin fibroblasts, newborn foreskin was trimmed of fat and twice washed in calcium-free Dulbecco's Phosphate-Buffered Saline (DPBS) for a few minutes and then incubated in 2.5% trypsin solution (Gibco, Grand Island, N.Y.) with 1 mM ethylenediamenetetraacetic acid (EDTA) for 15 minutes. The foreskin sample was then cut into approximately 1 mm pieces and digested for 1 hour in 500 units/ml bacterial collagenase (Type II, Cooper, Malvern, Pa.), with 200 units/ml penicillin G, 200 µg/ml streptomycin, and 2.5 µg/ml amphotericin B, in DPBS, at 37° C. and under periodic agitation (every 10 minutes). Undigested tissue was removed by allowing it to settle at the bottom of a centrifuge tube while the cell suspension is removed. Cells were pelleted by centrifugation, resuspended in culture medium, and placed in a Falcon T75 tissue culture flask. Approximately 1 million cells were obtained from 2 foreskins by this procedure. Cells were maintained in 5% CO at 37° C. The culture medium used for the primary culture was Dulbecco's Modified Eagle Medium (DMEM, Gibco) supplemented with 10% calf serum, 200 units/ml penicillin G, 200 µg/ml streptomycin, and 2.5 µg/ml amphotericin. Culture medium was changed every 3 days. The primary culture was subcultured after 2 weeks when cells grew confluent.

Cells were passed by trypsin disaggregation upon confluence. Pass 5 cells were used in constructing oriented tissue-equivalents. At pass 2 and pass 4, cells were cryogenically preserved in DMEM with 10% dimethyl sulfoxide (DMSO) and 20% calf serum and thawed as needed. The density of cells in the preservation medium was between 1 to 2 million cells per ml. Cells were kept frozen for no more than 18 months. The culture medium used for subcultures was DMEM with 10% calf serum. Culture medium was changed every 3 days.

Extraction and Purification of Collagen From Rat Tail Tendon

Rat tail collagen was used to form the collagen matrix of oriented tissue-equivalent. The rat tail collagen solution was extracted from rat tail tendon, with 100–200 mg of purified collagen per rat tail. Tendons were pulled from each tail with hemostats and carefully dissected to exclude other tissue. The tendons were then placed in 1% NaCl solution and washed once with 1% NaCl and twice with water. The tendons that were contaminated with muscle or bone were discarded. The tendons were placed in 0.5M (3%) acetic acid at the ratio of 200 ml per tail. (Approximately 10 parts with w/v 0.5 M acetic acid). The mixture was stirred for 24 hours at 4° C.

All the following steps were performed at 4° C. After 24 hours of stirring, the mixture was filtered through several layers of cheese cloth using a Buchner funnel. The mixture was centrifuged at 12000 g (9000 rpm in Sorval GS-3 rotor, bottles filled to less than ½ capacity) for 2 hours. The pellet formed at the bottom of the tubes was discarded. The approximate collagen content was determined by lyophilyzing and weighing a 5 ml aliquot of the supernatant.

The collagen was precipitated by dripping ⅓ volume of 30% NaCl solution into the supernatant over a 30 minute period under constant stirring. This was allowed to stand for 1 hour. The mixture was then centrifuged at 4000 g (5000 rpm in Sorval GS-3 rotor, or 4450 rpm in IEC 845A rotor) for 30 minutes. The supernatant was then discarded. The pellet was washed once with 5% NaCl 0.1M (0.6%) acetic acid. It was again centrifuged to reconsolidate the pellet. This last step was repeated once. Finally the pellet was resuspended in 0.1M (0.6%) acetic acid with about 2 hours of stirring. The volume of acetic acid used depended upon the desired collagen concentration which should not exceed 4 mg/ml for ease of handling.

The next step involved dialyzing the solution against 1 mM HCl enough times for 100,000 fold dilution of original solutes. For example, dialyze against 9× volume 5 times. The dialysate was changed every 12 hours. The solution was then centrifuged at 12,000 g for 2 hours. The pellet was discarded. To sterilize the solution 3/1000 volume of chloroform was added and allowed to stir in a bottle with a loose cap for 48 hours. The solution was diluted with 1 mM HCl, if dilution was necessary. The low HCl molarity allowed the collagen solution to be neutralized by the 44 mM bicarbonate buffer in DMEM, without adding NaOH. The neutralization of collagen resulted in its precipitation causing the mixture to gel. The final solution was stored at 4° C.

The final collagen concentration was determined by weighing a lyophylized aliquot. The concentration of collagen solution used throughout the examples was 2.4 mg/ml.

Casting Oriented Collagen Gels

The formation of an oriented tissue-equivalent involved the sequential addition of the following components: 36% twice concentration Dulbecco's Modified Eagle Medium (DMEM), 8% NuSerum (Collaborative Research, Bedford Mass.), 1.0% Ascorbic acid supplement (5 mg/ml), 0.5% antibiotic solutions, 0.5% Cupric sulfate supplement (0.26 mg/ml), 35% collagen solution, and 20% cell suspension (1.7 million cells in 1X DMEM with 10% NuSerum). All of the above components were maintained at 4° C. prior to mixing except for the cell suspension, which was maintained at room temperature. Components were mixed in a Erlenmeyer flask and then pipetted into 4 glass dishes (Pyrex 80×40 mm crystallizing dish, coated with a water repellent, Prosil-28, SCM Chemicals, Gainsville, Fla., to retard cell adhesion). Each dish received 13 ml of this mixture. It was discovered that the cells were unable to maintain proper pH levels (pH 7.4) in DMEM with glucose for long periods of time (2–3 days). Thus, DMEM with glucose was replaced with glucose-free DMEM with 10 mM fructose throughout the period of cell culture. Two porous polyethylene posts (Cat. #5531, Porex, Fatburn, Ga.), ¼" diameter, 7 mm in height, and a ⅛" central core, held at 2 cm apart were placed in the center of the glass dish. The posts were held by a polysulfone spacer, ⅛" thick, which sat above the fluid level of the culture dish.

The first step in the casting of an oriented tissue-equivalent involved autoclaving the porous polyethylene posts in a large beaker of water. Subsequently, the posts/spacer were transferred to a culture dish containing 15 mls of fresh 0.5 mg/ml polylysine solution. The polylysine was used as an adhesive to increase the affinity of the cells for the polyethylene posts. The posts were allowed to soak in this solution for 5 minutes. The procedure must be followed with care to avoid contact of the polysulfone backing with the polylysine solution. The posts/spacer were then washed with sterile water and then stored in a beaker of Hanks Buffered Salt Solution (HBSS).

Culture dishes were placed on bioassay trays with a maximum of four dishes per tray. Each of the culture dishes was rinsed with 10 ml of DMEM to facilitate the spread of the collagen solution on the culture dish. The post/spacer were then transferred to the culture dishes and aligned in the center with the aid of a short polysulfone rod glued to the dish. The rod fits into the ⅛" central core drilled in the center of the porous post.

The gels were cast in batches of 100 ml or less. Thus, an ideal number of gels to make from each batch is four, requiring only 68 mls of the gel recipe. To begin this procedure, 2X DMEM, NuSerum, fungizone, copper sulfate, and ascorbic acid (Vitamin C) were added proportionally to a 250 ml flask.

Fibroblasts were then trypsinized using a 0.1% trypsin and 0.4 mM EDTA solution to obtain a cell suspension. The viable cell density was calculated using a hemocytometer. The cell suspension was diluted appropriately and the needed volume was aliquoted to a separate tube.

The appropriate volume of collagen was quickly pipetted to the other gel components in the 250 ml flask. The flask was swirled during this process. The aliquot of cell suspension was promptly added. The mixture was mixed well by swirling. 13 ml of the mixture was then added to each of the four culture dishes. The cell-collagen mixture was warmed to 37° C. to form a gel. Finally the tray of dishes was stored in the incubator.

By gross inspection, the contraction process of the gel by the fibroblasts was mostly complete after one week in culture. Cell traction on the collagen network contracted the gel to less than 2% of its original volume, eventually forming a "dumbell shaped" band around the two posts. The culture media was changed every 2 days. The culture media used was DMEM supplemented with 10% NuSerum, 21 μM copper, 840 μM sulfate, and 50 μg/ml freshly dissolved ascorbic acid. Copper is a cofactor for lysyl oxidase, the enzyme responsible for collagen crosslinking. Sulfate is necessary for glycosaminoglycan synthesis and ascorbic acid increases collagen biosynthesis in vitro and is a cofactor for prolyl and lysyl hydroxylase. These media changes are done with care to avoid damage or serious disturbance to the gel.

Changes in Composition and Dimensions of Ligament-Equivalent

The wet weight reflects the total volume of the oriented tissue-equivalent. The wet weight of the oriented tissue-equivalent was obtained following mechanical testing in the mechanical testing apparatus. Prior to weighing, the oriented tissue-equivalents were immersed in DPBS for two washes of 15 minutes each. The oriented tissue-equivalents were then blotted dry on filter paper and the wet weight measured on an electronic scale. Subsequently, the oriented tissue-equivalents were lyophylized for at least 48 hours and the dry weight was obtained. The weight of solutes in the culture medium was subtracted from the lyophylized weight of gels to give an adjusted dry weight that corresponds to the insoluble components in the cells and matrix. The solid fraction stabilized at approximately 6%.

The volumes and the dry weights of the oriented tissue-equivalent were measured on day 7, 14, 21, 28 and 42 after fabrication. When initially cast, the oriented tissue-equivalents had a volume of 13 ml, which was equivalent to a wet weight of 13 grams. Volume contraction was rapid during the first week, after which the wet weight decreased to 298 mg, 2.3% of the initial volume after 6 weeks.

The content of solid material in the oriented tissue-equivalents showed only a slight decrease over time. The cell population actually increased during culture, thus indicating that degradation and loss of the extracellular matrix outstripped synthesis. Further, 13 mg of soluble collagen was used in the initial casting of the oriented tissue-equivalents. The adjusted dry weight of the oriented tissue-equivalents 3 days after casting was only 11.7 mg, thus, a small proportion of collagen failed to be incorporated into the extracellular matrix.

The dry weight to wet weight ratio of the oriented tissue-equivalent after 6 weeks in culture was 6.6%, roughly ⅓ that of natural soft connective tissue. For example, skin is 50–70% water. Harkness, R. D., *Biophysical Properties of Skin*, (Ed. Elden H. R), pps 393–436, John Wiley and Sons, N.Y. (1971). Rabbit medial collateral tendon contains 64% water. Woo, S. L. Y., and Buckwalter, J. A., Eds, *Injury and Repair of Muscoluskeletal Soft Tissues,* American Academy of Orthopedic Surgeons, Park Ridge, Ill. (1988).

EXAMPLE II: Mechanical Properties of Oriented Tissue-Equivalent

Mechanical Testing Apparatus

A mechanical testing apparatus as illustrated in FIGS. 3 and 4 was employed. The mechanical testing instruments were mounted in a temperature and gas composition controlled incubator (model #31483, GCA Corp., Chicago, Ill.), capable of maintaining a tissue culture environment. The apparatus was equipped to handle 3 samples per experimental run. The oriented tissue-equivalents were fastened into loading chambers by the two posts around which they had formed an adherent band. The upper post was clamped to a shaft connected to a computer controlled step motor (model #M578331, Compumotor Corp., Petaluma, Ga.) which functioned to stretch or compress the oriented tissue-equivalents, while the lower post was connected to a fixed platform. The oriented tissue-equivalents were entirely immersed in culture medium, which was continuously recirculated with a peristaltic pump (Model #7520-35, Cole-Parmer, Chicago, Ill.).

Force transducers (Model LC2 with UL4-0.5 accessory, Gould Inc., Oxnard, Calif.) were used to determine the force generated by the oriented tissue-equivalents. A linear variable differential transformer (LVDT) (Model #0244-0000, Trans-Tek Inc., Ellington, Conn.) was used to determine the displacement of the oriented tissue-equivalent. The tissue length was controlled with the step motor, which was programmed to generate displacement waveforms of ramp, steps, and sinusoids with a maximum velocity of 1 cm/sec. Transducer signals were amplified (2000X V/V), low-pass filtered through a 3-pole bessel type filter with cutoff frequency at 15 Hz, sampled by an analog-to-digital converter (DT2801, Data Translation Inc., Marlboro, Mass.) and recorded on a Wells American A-Star computer (Wells American Corp., West Columbia, S.C.).

In general, tissue models were mounted and maintained at the resting length for at least 30 minutes before mechanical manipulations. It was determined that 30 minutes was sufficient for equilibration of the temperature inside the incubator; a condition necessary for accurate load cell operation. The following sections describe in detail the features of the mechanical testing apparatus which provided a controlled environment for measuring the forces developed by the oriented tissue-equivalents.

Environmental Controllers:

Gas Control

The mechanical testing apparatus was equipped to provide as many as three different gases simultaneously into the incubation chamber (volume of 5.3 cubic feet). In the following examples, the composition of the gases in the incubation chamber was 5% $CO_2$ and 95% air. Each gas had two flowmeters; one controlled the flow rate during normal operation, while the other controlled the flow rate during "purging". The process of purging replaced the incubator gas volume and gas composition. This function was necessary if the door to the apparatus was left ajar for any length of time. The system included a sampling tube which was used in conjunction with a Fyrite meter to test the $CO_2$ concentration within the chamber.

Temperature Control

A heating convection unit controlled by a temperature regulator (Cole-Palmer Instrumentation model 2156) maintained the incubator chamber temperature at 37° C. The heating unit used a high speed fan (5"×5") to circulate the incubator gases over a 200 watt light bulb covered with fins of aluminum foil. The aluminum fins were heated by the light bulb, and subsequently warmed the air which entered via a 7.5 inch$^2$ port and then returned to the incubator. The high speed fan and aluminum foil covered light bulb were encased in a rectangular plexiglass box (5"×5"×11") which sat at the bottom of the incubator chamber where the air was coldest. The power of the light bulb was controlled by the temperature regulator. As the temperature approached 37° C. (usually attained within 25 minutes starting from room temperature 25° C.), the power of the bulb decreased. The exact temperature inside the chamber was displayed on a LED panel which was connected to a thermistor residing within the chamber.

Computer Controlled Step Motor

The mechanical testing apparatus actuator was connected to a precision lead screw driven by a high precision computer controlled step motor (Model M578331, Compumotor Corp., Pataluma Calif.). The motor takes three TTL compatible digital inputs: speed, direction and remote shutoff. The direction and speed inputs were provided by programs on a Motorola 68000 based single board computer.

The speed input controlled the angular velocity of the motor. For every pulse sent to this input, the step motor revolved 1/50,000th of a revolution. Thus, the actuator had a minimum displacement of $5 \times 10^{-2}$ µm. The speed was proportional to pulse rate. A maximum pulse rate of 0.33 mHz limited the maximum speed of the actuator to 3 cm/second. It is recommended that the actuator not be driven faster than 1 cm/second.

The direction input determined the direction the motor would turn. An input of 0 volts would cause the motor to rotate clockwise and therefore move the actuator upward. A direction input of 5 volts would move the actuator downward.

The actuator and motor were protected from being inadvertently driven up into the roof of the incubator or driven down into the loading chambers which contained the oriented tissue-equivalents. The incubator was outfitted with two remote shut-off switches which when activated stop the step motor. A remote shutoff input of 0 volts would allow normal operation, while an input of 5 volts would automatically stop the motor. These switches were strategically located and could be activated before damage could occur to the apparatus.

Loading Chambers

The loading chambers secured the oriented tissue-equivalents for mechanical loading by the computer controlled actuator. The loading chambers were made of polysulfone which is easily machined and can be autoclaved repeatedly. Each loading chamber was comprised of three components: an outer vessel, an inner vessel, and a shaft. (See FIG. 4)

The outer vessel can hold a maximum of 50 ml of culture media and was secured to the platform by a brass screw. A peristaltic pump was connected to the loading chambers to recirculate the culture media. The inner vessel was designed to secure one end of the oriented tissue-equivalent using a polysulfone pin. It was slotted to provide easy insertion and removal of the oriented tissue-equivalent. The inner vessel was fastened by six stainless steel screws along the upper perimeter of the outer vessel. Upon tightening the screws, the inner chamber was secured in the center of the outer chamber.

The opposite end of the oriented tissue-equivalent was secured to the shaft with a polysulfone pin. The shaft was attached to the actuator, thus providing for the stretching or compressing of the oriented tissue-equivalent. The shaft was initially secured to the inner vessel by two stainless steel screws, thus allowing for the insertion of the oriented tissue-equivalent without altering its original length. After all the components were properly secured, the two stainless screws were removed allowing the shaft to be moved via the computer controlled step motor.

Transducers:

Load Cells

The three load cells (Gould Electronics model UC2) measured the forces generated by the oriented tissue-equivalents. The load cells were mounted on 0.5 pound adapters which attached to the actuator and the shafts of each loading chamber. With the adapters, the load cells can measure ±0.5 pounds at a displacement of ±0.06 mm. The load cells required a 5 volt power supply. Their full-scale output voltage was ±6 mv/v, thus with a 5 volt power supply, the maximum output voltage is +30 mv. Because the load cells were highly sensitive to changes in tension and compression, a high precision signal conditioning module (Analog Devices model 2B31) served as both a power supply and amplifier for the load cells. The module can amplify the output signal of the load cell by a factor of 50, 110, 240, or 350. For measuring oriented tissue-equivalent forces, the maximum gain of 350 was used. The signals were then directed to a second amplifier with biase control and a fixed gain of ten. The signals were then sampled and converted to 12 bit quantities by an analog-to-digital converter. The digital signals were collected by an IBM-PC AT.

Linear Variable Differential Transformer

The linear variable differential transformer (LVDT) measured the displacement of the actuator. It has two components: a metal rod and an inductor. They were housed in the aluminum step motor case located above the incubator chamber. The metal rod which was attached to the actuator rod moves vertically as the actuator moves through the securely fastened inductor. The output signal changed as the metal rod moves at the rate of 5.0 volts/cm. This output signal was a differential voltage which was fed through a unit gain op-amp and then collected by the IBM-PC AT via the analog-to-digital converter.

Data Acquisition

As mentioned above, an IBM AT via an analog-to digital-converter (Data Translation DT-2800) collected signals from the three load cells and the LVDT. The A/D converter has a range of ±10 volts and converted these values into 12 bit quantities. Channel 4, 5, 6, 7 of the A/D converter were wired to the LVDT, load cell 1, 2, and 3, respectively. The A/D converter was used in conjunction with ASYST (software tailored for data acquisition and analysis, Macmillan Software, Rochester, N.Y.).

During an experimental run, a total of 512 points were obtained from each source (i.e., load cell #2). These points were the result of averaging a group of successive signals which were sampled at the rate of once every 24 msec. The number of signals which were averaged to obtain one of the 512 points was determined by the period of the experimental run. For example, during an experimental run which lasted for 80.4 seconds, a total of 157 msec was available for collecting signals and calculating the mean average to obtain one of the 512 points. Within the 157 msec duration, a total of 20 samples was collected requiring 140 msecs and an additional 17 msec was needed for the software to implement the averaging of the routine.

The data from the LVDT and the three load cells were stored and manipulated as ASYST data structures.

Mechanical Loading Protocol

In each of the following examples, three oriented tissue-equivalents formed as described in detail in Example I, were mounted in the incubator-mechanical testing apparatus. The two posts around which an oriented tissue-equivalent had contracted were clamped to a shaft and an inner vessel of the loading chamber. The shaft and inner vessel were locked into position so that the oriented tissue-equivalent maintained its resting length, and the spacer that held the posts in place was removed. The shaft and inner vessel were then immersed in a loading chamber filled with approximately 50 ml of culture media and mounted on the mechanical testing apparatus. The shaft was connected to the step motor-driven actuator and the inner vessel was connected to a fixed platform in the testing apparatus. The lock between the shaft and the inner vessel was released so that the oriented tissue-equivalent length could be controlled by the step motor. Silicone rubber tubing from the media filled vessel was connected to a peristaltic pump and the media was recirculated at approximately 10 ml/minute.

After mounting was completed, 30 minutes were allowed for gas composition and temperature to equilibrate inside the incubator. A −10% strain was maintained for 10 minutes for mechanical equilibration. The oriented tissue-equivalents were then-stretched 110% (2.1 cm) at the strain rate of 0.05% per second (10 µm per second). The strain and the tensile load on the 3 mounted oriented tissue-equivalents were sampled every 24 msec. Every consecutive 162 samplings were averaged to give 512 recorded data points for every load and strain channel.

Figure 9:
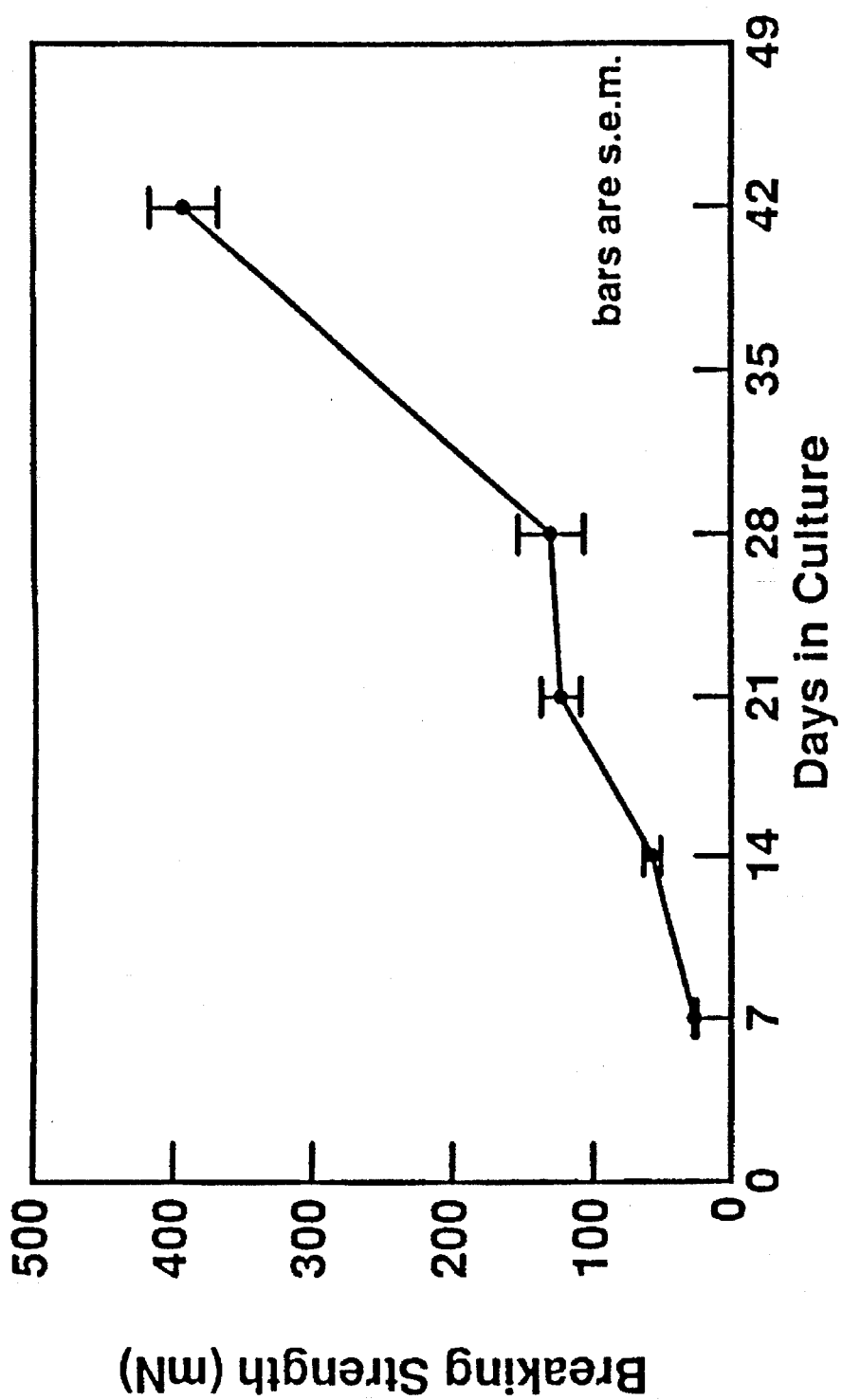
FIG. 9 is a graphic representation of breaking strength in an oriented tissue-equivalent.
Figure 10:
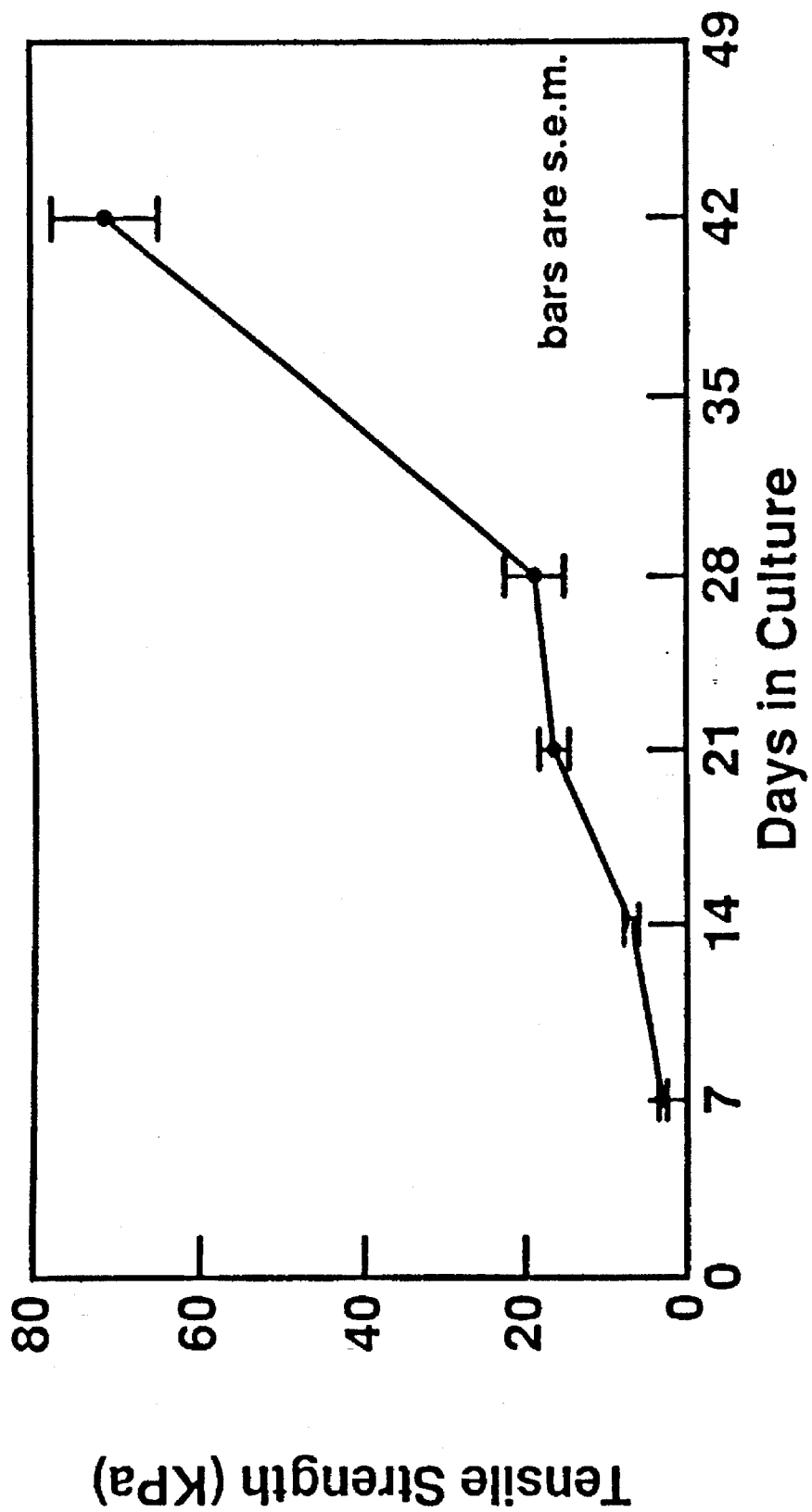
FIG. 10 is a graphic representation of tensile strength of an oriented tissue-equivalent.

EXAMPLE III: Breaking Strength and Incremental Young's Modulus of Oriented Tissue-Equivalent As shown in FIG. 9, the breaking strength of the oriented tissue-equivalent increased monotonically with culture time between 1 and 6 weeks. The estimated tensile strength (stress at failure) increased with the same trend as the breaking strength, as the change in the cross-sectional area of the oriented tissue-equivalent over time is small. This trend is diagrammed in FIG. 10.

Figure 11:
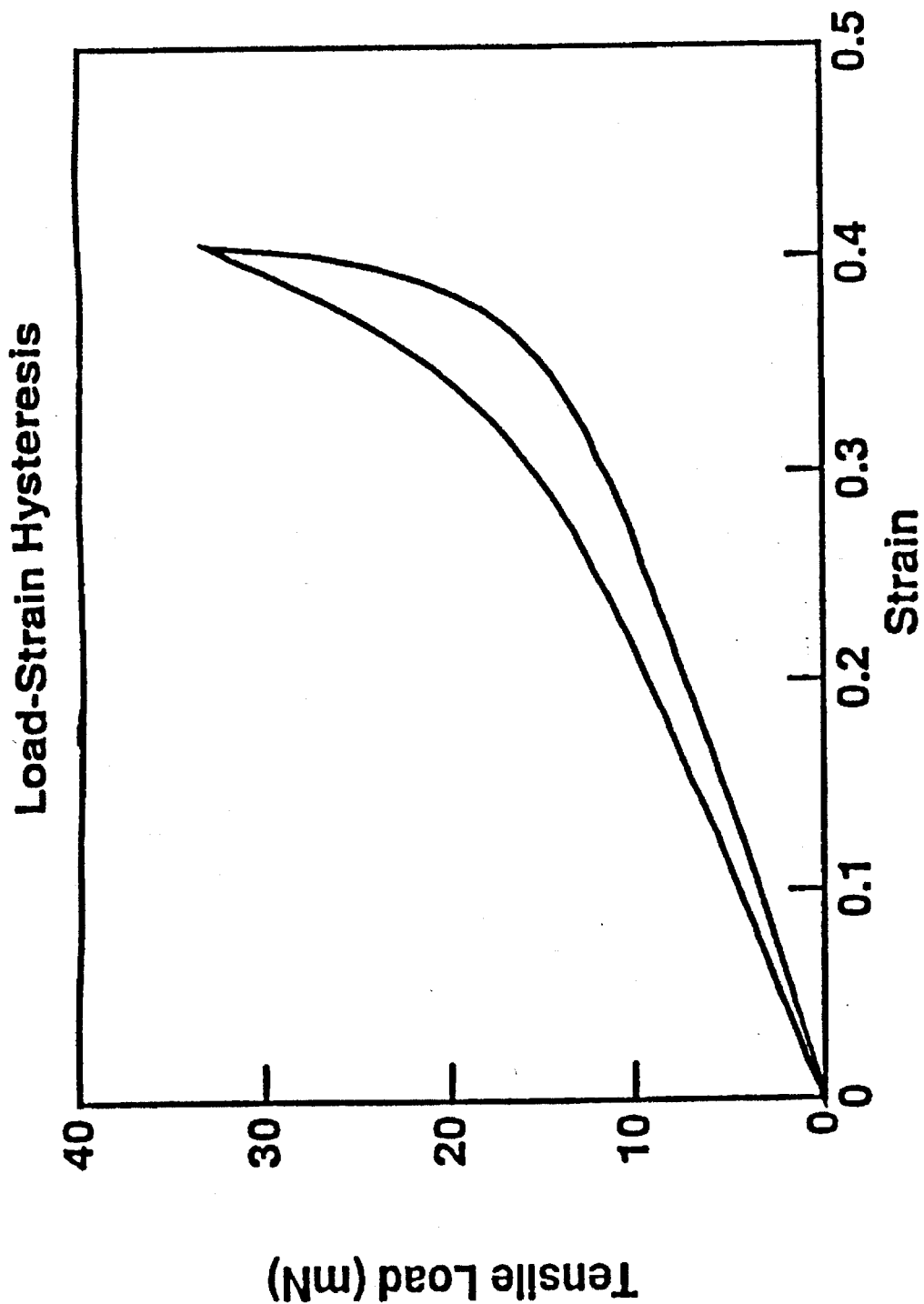
FIG. 11 is a graphic representation of an average hysteresis curve of a conditioned oriented tissue-equivalent.

The breaking strengths of the oriented tissue-equivalents were determined by stretching the samples at a rate of 10 µm/second, or an estimated strain rate of 0.05%/second. At this strain rate, load-release cycles of the material still show significant amounts of hysteresis. Thus, the tests were not conducted at a truly quasistatic strain rate. However, lowering the strain rate would increase errors due to metabolic changes in the living tissue, and errors due to instrument drift. FIG. 11 shows the average hysteresis curve of a conditioned oriented tissue-equivalent. Six oriented tissue-equivalents at three weeks culture were preconditioned by 3 cycles of stretch release. The oriented tissue-equivalents were then subjected to cyclic stretch-release at the strain rate of 0.05%/second (10 µm/second) between 0% and 40% strain.

Figure 12:
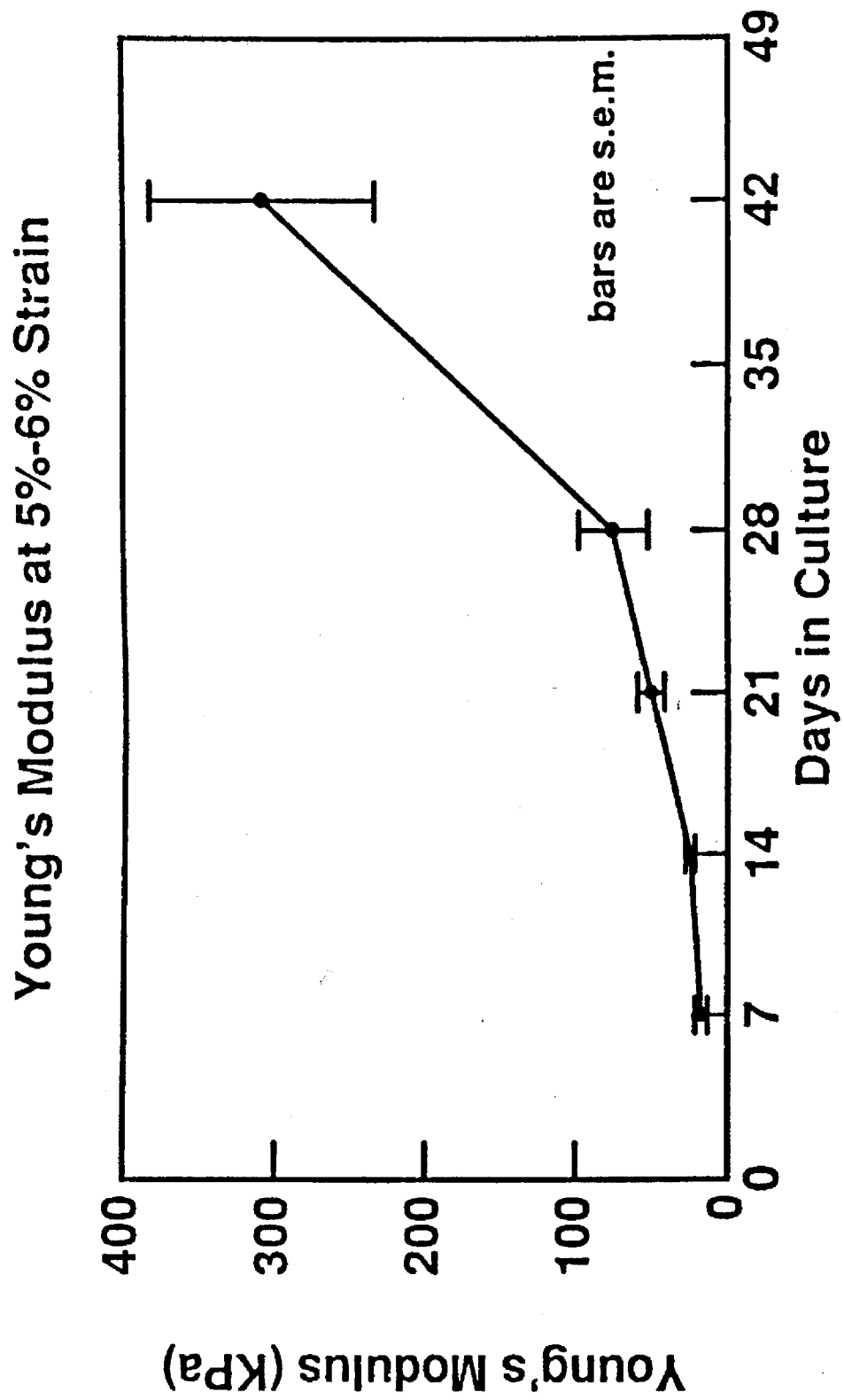
FIG. 12 is a graphic representation of incremental Young's modulus at 5–6% strain in an oriented tissue-equivalent.

FIG. 12 shows that the estimated incremental modulus of the oriented tissue-equivalent increased monotonically with time in culture.

EXAMPLE IV: Cell Proliferation in Oriented Tissue-Equivalents

The DNA content of a papain digest of an oriented tissue-equivalent prepared as described in Example I, was measured by a fluorometric assay described by Labarca, C. and Paigen, K., *Anal. Biochem.*, 102: 344–352 (1980).

The stock solution was diluted to 0.125 mg/ml in phosphate-buffered saline (PBS)(⅔ physiologic osmolarity, pH 6.0) with 3.5 mM EDTA and 4.5 mM cysteine. 3 ml of papain solution (type III, Sigma Chemicals, St. Louis, Mo., 25 mg/ml; 24 units/mg) was added to each oriented tissue-equivalent previously lyophilized as described above in the weighing procedure and stored in an airtight tube (0.2 to 0.4 ml papain solution/mg dry tissue). The mixture was put in a 60° C. water bath for at least 12 hours.

50 µl of papain digest was pipetted into a cuvette (Centaur, West Sparks, Nev.) and 2 ml of dye solution (Hoeschst 33258, diluted to 0.1 µg in a solution containing 10 mM Tris, 1 mM EDTA, 0.1 mM NaCl, and adjusted to pH 7.4) was then added to each cuvette. After 20 minutes, the fluorescence over reference ratio was read at the emission wavelength of 458 nm, with the excitation wavelength set at 365 nm (SPF 1000C, SLM Instruments). The assay was calibrated using the DNA standard, with the cell standard used as a check. The DNA standard was Type I DNA from calf thymus purchased from Sigma, (nominally 100 µg/ml solution in PBS with 125 mM $MgCl_2$, pH 7.0) and the concentration was determined by absorbance at 260 nm. The cell standard was prepared from subcultured fibroblasts trypsinized at confluence and the cell count was obtained by hemacytometer. The cells were papain digested at $10 \times 10^6$ cells/ml, with dilutions ranging from $0.1 \times 10^6$ cells/ml to $10 \times 10^6$ cells/ml. The specificity of the assay was tested with DNAse treated samples of papain digest. 1 ml of papain digest was mixed with 1 ml of DNase solution and allowed to react for 30 minutes at room temperature. The DNAase solution was prepared from deoxribonuclease I Type IV from Sigma. 100 µg/ml was used in PBS with $MgCl_2$ added up to 125 mM concentration, and adjusted to pH 7.0.

Figure 13:
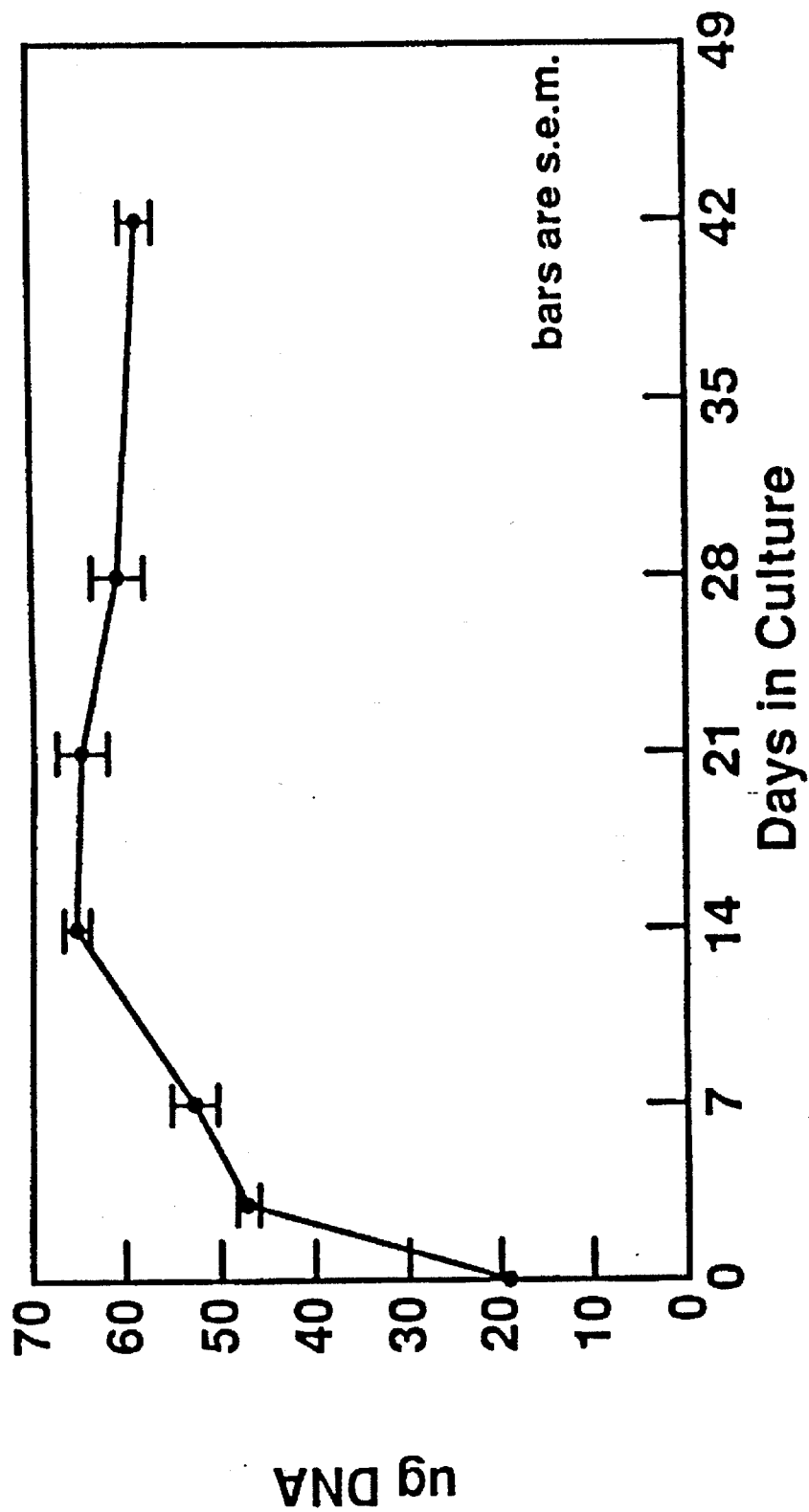
FIG. 13 is a graphic representation of DNA incorporation in an oriented tissue-equivalent versus days in culture.

As shown in FIG. 13, results demonstrate that the DNA content of the oriented tissue-equivalent triples during the first 2 weeks and thereafter actually shows a small decline. The decrease may be attributed to cell death or emigration of cells from the collagen matrix onto the surface of the culture dish. The surface of the culture dish became populated with cells after the first week, despite the coating of the dish surface with organosilane, a water repellent material.

These results are consistent with the results of others who described the rate of tritiated thymidine incorporation in adventitial fibroblast-populated collagen lattices peaked between days 2 and 7 and thereafter remained at a very low level. Further, it has been reported that collagen lattices seeded with higher cell density have lower proliferative activity, indicating that cell proliferation is limited by the density of cells in the fibroblast-populated collagen lattices. Weinberg, C. B., and Bell, E., *Science*, 231: 397–400 (1985).

Figure 14:
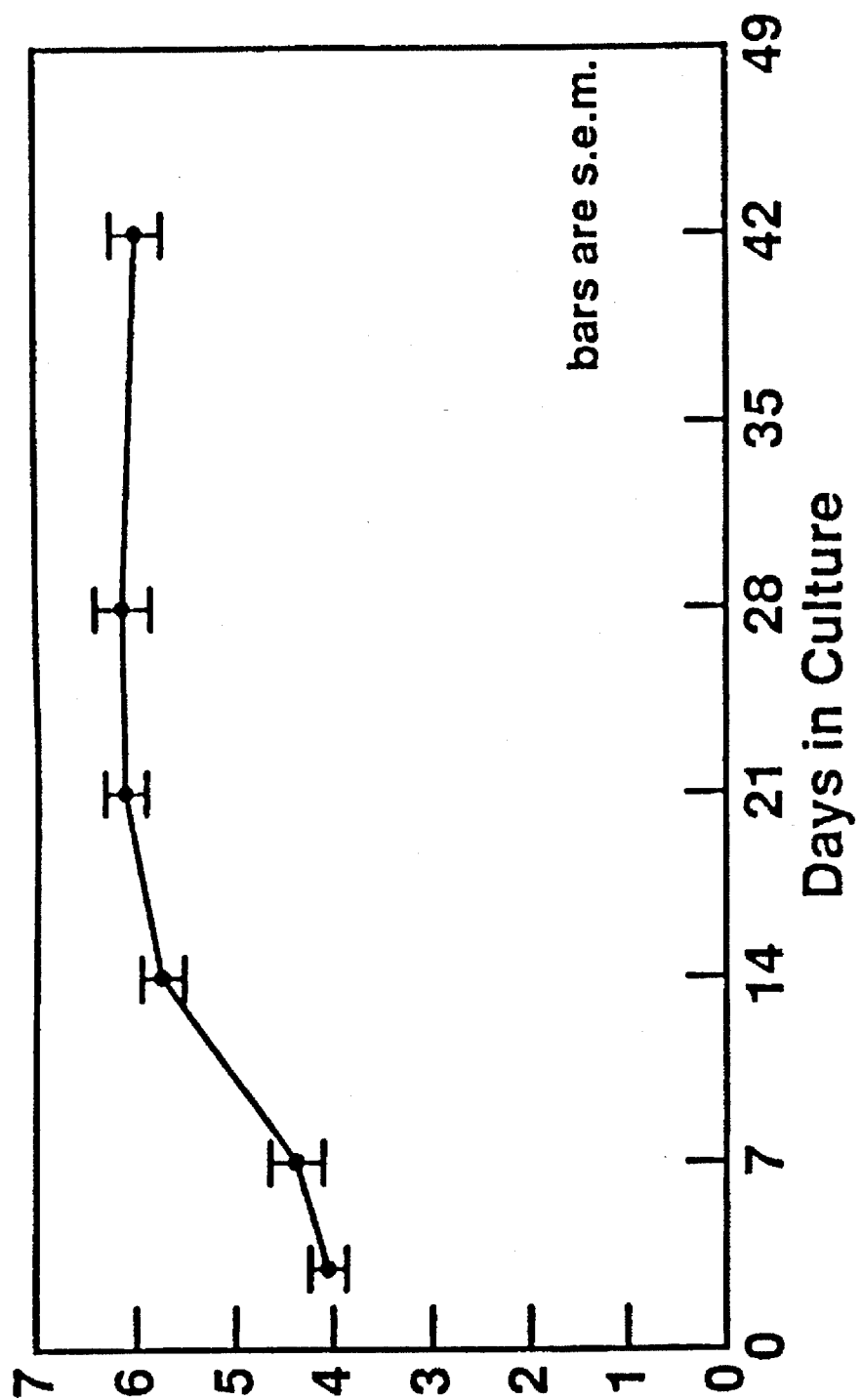
FIG. 14 is a graphic representation of the ratio of the amount of DNA to the amount of solid material in the oriented tissue-equivalent versus days in culture.

As shown in FIG. 14, the cell density of the oriented tissue-equivalent, when normalized against the dry weight of the oriented tissue-equivalent, reached a plateau after 2 weeks. The eventual value of 6 µg DNA per mg dry weight is comparable to that in tendon 7.7 µg/mg. Franklin, T. J., et al., *J. Lab. Clin. Med.*, 108:103–108 (1986).

EXAMPLE V: Collagen Cross-linking in Oriented Tissue-Equivalent

To determine the importance of lysine-derived collagen crosslinking to the mechanical properties of the oriented tissue-equivalent, two groups of 6 oriented tissue-equivalents were prepared as described in Example I, and incubated for 3 weeks. One group was incubated in the presence of 0.5 mM BAPN. The load-strain relationship was then measured. Following the mechanical testing, wet weight was obtained. Oriented tissue-equivalents were then washed twice with sterile PBS for 15 minutes per wash. Subsequently, they were lyophilized for at least 48 hours and the dry weight was obtained. The samples were papain-digested. DNA and glycosaminoglycan contents of the papain digests were assayed.

BAPN had a dramatic effect on the mechanical properties of the oriented tissue-equivalent. Table II shows that both the breaking strength and the estimated incremental Young's Modulus was significantly lower in the BAPN-treated group when compared with the control. At 3 weeks, the BAPN-treated group actually had lower breaking strength and incremental Young's modulus than was measured in the untreated group after 1 week. The strain at failure of the BAPN-treated group was significantly higher, thus indicating that although uncrosslinked collagen fibrils yielded more easily, they remained intact over a larger strain range.

TABLE II

|  | Tensile Load at Failure (mN) | Estimated Incremental Young's Modulus (KPa) | Strain at Failure |
|---|---|---|---|
| BAPN | 21.8 ± 0.88 | 7.6 ± 0.7 | >0.99 ± 0.02 |
| Control | 128.6 ± 13.3 | 70.7 ± 11.2 | 0.693 ± 0.03 |
| Significance | p < 0.001 | p < 0.001 | p < 0.001 |

EXAMPLE VI: Effect of Growth Transforming Factor Type β on Oriented Tissue-Equivalent Transforming growth factor type β (TFG-β) has been shown to induce the formation of granulation tissue in vivo and increase collagen formation in vitro. Roberts, A. B., et al., *Proceedings of the National Academy of Science*, 83:4167–4171 (1986). To test whether TFG-β may be a useful agent for increasing extracellular matrix biosynthesis and thereby increasing the mechanical strength in the oriented tissue-equivalent, its effects on incorporation of protein and sulfated glycosaminoglycan into the extracellular matrix of the oriented tissue-equivalent were measured with radiolabels.

Oriented tissue-equivalents were prepared as before (Example 1), with the following exceptions:

A smaller volume (6 ml) of collagen gel was cast in a smaller dish (60 mm diameter glass dish).

All items that were to come into contact with the culture media (dishes, porous posts, and spacers) were coated with AquaSil siliconizing fluid (cat # 42799, Pierce, Rockford, Ill.) to prevent adsorption of TFG-β.

Oriented tissue-equivalents were cultured for 7 days in standard culture media. On day 8, oriented tissue-equivalents were incubated in media supplemented with 0.5 mM proline for 20 hours. Prior to radiolabelling, oriented tissue-equivalents were washed once in DPBS for 5 minutes and twice in serum-free culture media for 15 minutes.

Oriented tissue-equivalents were then placed in 4 different culture media in the presence of radiolabels. 5 ml of labelling media was added to each oriented tissue-equivalent. The basic labelling media is DMEM without glucose, supplemented with 10 mM fructose, 21 μM copper, 840 μM sulfate, 50 μM ascorbic acid, 0.5 mM cold proline, 5 μCi/ml $5^3$H-proline, and 10 μCi/ml $^{35}SO_4$. Different supplements were present in each of the 4 groups:

1. Control group: no addition
2. NS group: 10% NuSerum (Collaborative Research, Bedford, Mass.) was added
3. TFG-β: 10 ng/ml TFG-β (cat # 40039, Collaborative Research) was added
4. TFG-β + NS: both 10 ng/ml TFG-β and 10% NuSerum were added.

After 20 hours of incubation, labelled media was replaced by cold DPBS to stop further radiolabel incorporation. Oriented tissue-equivalents were washed three times in DPBS for 40 minutes each time to remove free label. Oriented tissue-equivalents were then digested in 3 ml of 3 mg/ml collagenase (Type II, Cooper, Malvern, Pa.) in DPBS at 37° C. Cells in the digests were pelleted by centrifugation. Duplicate 100 μl aliquots of the supernatant were taken from each sample for scintillation counting.

Figure 15:
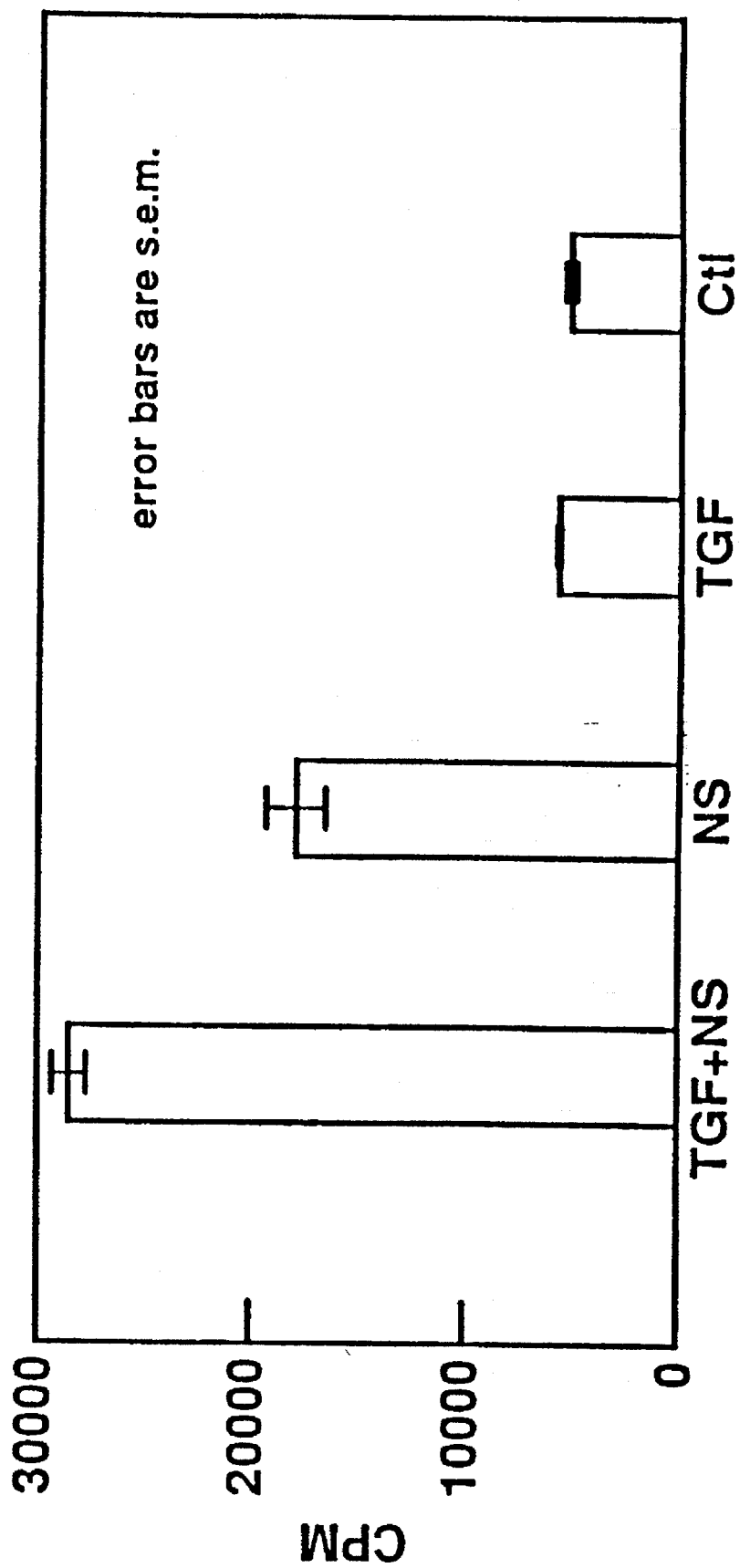
FIG. 15 is a schematic representation of $^3$H-proline incorporation into the extracellular matrix of an oriented tissue-equivalent cultured with TGF-$\beta$.
Figure 16:
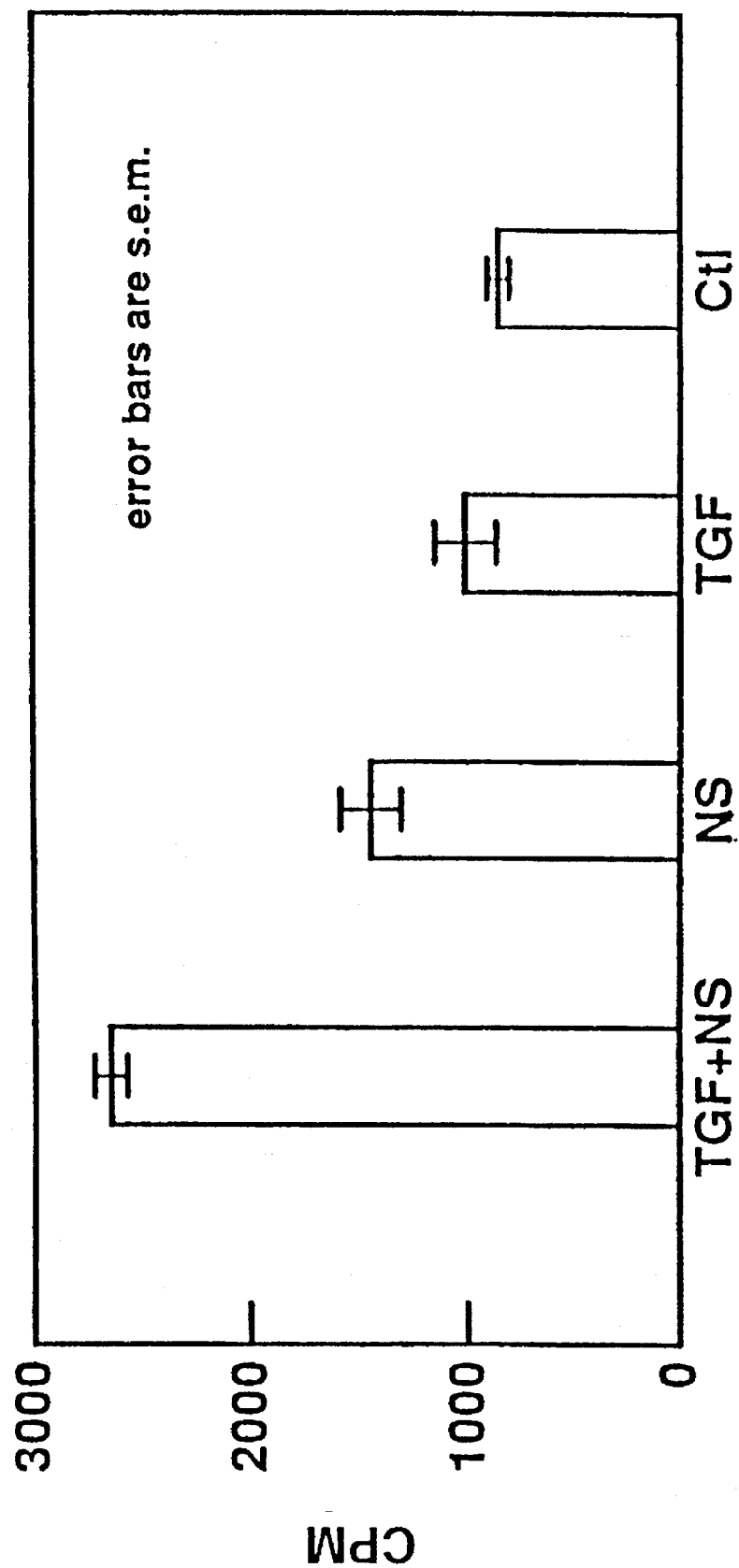
FIG. 16 is a schematic representation of $^{35}$S-sulfate incorporation into the extracellular matrix of an oriented tissue-equivalent cultured with TGF-$\beta$.

FIGS. 15 and 16 show that in the presence of serum, TFG-β increased incorporation of labelled proline into the extracellular matrix (ECM) by 60% (p < 0.01) and increased the incorporation of labelled sulfate into the ECM by 83% (p< 0.001), respectively. The incorporation of labelled proline and labelled sulfate is uniformly low in the absence of serum.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A method for producing connective tissue having a ligament configuration, comprising:
   forming a collagen gel having living fibroblasts dispersed therein;
   placing in said gel two porous posts;
   contacting the collagen gel with a crosslinking agent; and
   elevating the temperature of the gel to induce contraction of the gel by the fibroblast cells such that the gel orients along the axis between the two posts in a ligament configuration.

2. The method of claim 1 wherein the posts are comprised of polyethylene.

3. The method of claim 1 wherein the posts are comprised of porous hydroxyapatite.

4. A method of claim 1 additionally including the step of imposing a mechanical stimulus on the fibroblasts and collagen gel.

5. Connective tissue having a ligament configuration obtainable by the method comprising the steps of:
   forming a collagen gel having living fibroblasts dispersed therein;
   placing in said gel two porous posts;
   contacting the collagen gel with a crosslinking agent; and
   elevating the temperature of the gel to induce contraction of the gel by the fibroblast cells such that the gel orients along the axis between the two posts in a ligament configuration.

* * * * *